United States Patent
Kobayashi et al.

(10) Patent No.: US 8,449,609 B2
(45) Date of Patent: *May 28, 2013

(54) INSERTION DEVICE FOR INTRAOCULAR LENS

(75) Inventors: Kenichi Kobayashi, Ichikawa (JP); Shinobu Toyomane, Ichikawa (JP)

(73) Assignee: Staar Japan, Inc., Irifune, Urayasu-shi, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/818,048

(22) Filed: Jun. 17, 2010

(65) Prior Publication Data

US 2010/0256652 A1  Oct. 7, 2010

Related U.S. Application Data

(60) Division of application No. 11/940,815, filed on Nov. 15, 2007, now abandoned, which is a continuation-in-part of application No. 11/749,812, filed on May 17, 2007, now abandoned.

(30) Foreign Application Priority Data

| May 18, 2006 | (JP) | 2006-139560 |
| May 18, 2006 | (JP) | 2006-139561 |
| Jun. 2, 2006 | (JP) | 2006-155051 |

(51) Int. Cl.
   *A61F 2/16* (2006.01)

(52) U.S. Cl.
   CPC .................... *A61F 2/1662* (2013.01)
   USPC ...................................... 623/6.12

(58) Field of Classification Search
   USPC ............ 606/107; 623/5.11, 6.11, 6.12
   See application file for complete search history.

(56) References Cited

U.S. PATENT DOCUMENTS

| 4,402,308 A | 9/1983 | Scott |
| 4,765,329 A | 8/1988 | Cumming et al. |

(Continued)

FOREIGN PATENT DOCUMENTS

| DE | 19544119 A1 | 5/1997 |
| EP | 1360944 A2 | 11/2003 |

(Continued)

OTHER PUBLICATIONS

European Search Report dated Oct. 13, 2009, issued by the European Patent Office in the counterpart European Patent Application No. 09168075.1, p. 1-8.

(Continued)

*Primary Examiner* — Tuan V Nguyen
*Assistant Examiner* — Jonathan Miles
(74) *Attorney, Agent, or Firm* — John K. Fitzgerald; Fulwider Patton LLP

(57) ABSTRACT

An insertion device for an intraocular lens is disclosed which can prevent leakage of a liquid in the device and can house and store a lens as well as the liquid. The insertion device includes a main body including a lens housing portion that houses the lens and an insertion cylindrical portion that feeds the lens into an eye, a pushing shaft that moves the lens from the lens housing portion in the front end direction to push out the lens into the eye through the insertion cylindrical portion, and a lens holding member that holds the lens, and is placed in the lens housing portion. The lens housing portion has a shape that receives insertion of the lens holding member from the rear.

4 Claims, 33 Drawing Sheets

U.S. PATENT DOCUMENTS

| | | | |
|---|---|---|---|
| 5,222,972 | A | 6/1993 | Hill et al. |
| 5,616,148 | A | 4/1997 | Eagles et al. |
| 5,728,102 | A | 3/1998 | Feingold et al. |
| 6,059,791 | A | 5/2000 | Chambers |
| 2004/0243141 | A1 | 12/2004 | Brown et al. |
| 2010/0076450 | A1* | 3/2010 | Yoshida et al. ............... 606/107 |
| 2010/0082037 | A1* | 4/2010 | Kobayashi et al. ........... 606/107 |

FOREIGN PATENT DOCUMENTS

| | | |
|---|---|---|
| EP | 1360946 A | 11/2003 |
| EP | 1438929 A | 7/2004 |
| EP | 1481652 A1 | 12/2004 |
| JP | 2003-325568 | 11/2003 |
| JP | 2004351196 | 12/2004 |
| WO | 99/37247 A | 7/1999 |
| WO | 2004026377 A1 | 4/2004 |
| WO | 2005030097 A1 | 4/2005 |

OTHER PUBLICATIONS

European Search Report dated Oct. 21, 2009, issued by the European Patent Office in the counterpart European Patent Application No. 09168074.4, p. 1-7.

European Seach Report dated May 2, 2008, issued by the European Patent Office in counterpart European Patent Application No. 07120839.1, p. 1-4.

European Search Report date Jan. 16, 2009, issued by the European Patent Office in counterpart European Patent Application No. 07108353.9, p. 1-12.

* cited by examiner

INSERTION DEVICE FOR INTRAOCULAR LENS

This application is a divisional of U.S. application Ser. No. 11/940,815, filed Nov. 15, 2007, which is continuation-in-part of U.S. application Ser. No. 11/749,812, filed May 17, 2007, now abandoned, which claims foreign priority to Japanese Patent Application Nos. 2006-139560, filed May 18, 2006; 2006-139561, filed May 18, 2006; and 2006-155051 filed Jun. 2, 2006. Applicants claim priority to all of the applications in the chain.

BACKGROUND OF THE INVENTION

The present invention relates to an insertion device for inserting into an eye an intraocular lens that is inserted instead of a crystalline lens after the crystalline lens is extracted because of cataract or inserted into an eye in order to cure abnormal refraction.

In current operations for cataract, the central portion of the anterior capsule of an eyeball is ablated, a clouded crystalline lens is removed by an ultrasonic suction apparatus, and then an artificial intraocular lens (hereinafter simply referred to as a lens) is placed in the position of the removed clouded crystalline lens. When placing the lens in the eyeball, an operation method for inserting the lens into the eyeball through a small incision by using the flexibility of the lens and thereby deforming the lens, e.g. folding the lens into a small shape is the mainstream.

In the case of an operation, an insertion device is frequently used which deforms a lens set in a main body of the device into a small shape while moving the lens in the main body of the device by a pushing shaft and pushes out the lens into the eye from a front end opening of an insertion cylinder (nozzle) inserted into the incision. This insertion device is used not only for the operation of cataract but also for a lens inserting operation for an eyesight correction medical treatment.

When the lens is inserted into an eye by using the insertion device, a viscoelastic material such as sodium hyaluronate is introduced into the main body of the insertion device as a lubricant so that the lens is smoothly moved and deformed in the insertion device (see Japanese Patent Laid-Open No. 2004-351196). Moreover, the viscoelastic material has a function of spreading the space of the anterior chamber of the eye into which the lens will be inserted by being introduced into the eye through the insertion cylinder.

Further, it has been recently required to use inexpensive physiologic saline in place of the viscoelastic material.

However, when the main body of the insertion device is constituted by a plurality of components assembled to each other, for example, when a lens setting portion in the main body has a divided structure or an openable and closable structure, a liquid such as a viscoelastic material or physiologic saline leaks from a gap created at the assembled portion. The leaking liquid makes the insertion device slippery or soils the periphery of the device.

In the case of a conventional operation, a liquid is introduced into the insertion device immediately before the operation, which takes time and places a heavy burden on an operator or an assistant.

Further, even if the liquid such as a viscoelastic material or physiologic saline is introduced into an eye, a large amount of liquid leaking from a gap between an edge of an incision in the eye and an insertion cylinder (an amount of leakage outside the eye) prevents an increase in ocular tension and sufficient inflation of the anterior chamber.

To a pushing shaft, an elastic member such as rubber is frequently mounted for preventing a lubricant introduced into the main body from leaking from between an inner peripheral surface of the main body and the pushing shaft, and providing proper resistance (sliding feeling) to an operation of the pushing shaft.

In the conventional insertion device, the elastic member is secured to one or a plurality of points close to each other on the pushing shaft, and moved relative to the main body with the operation of the pushing shaft. This cannot prevent the pushing shaft from being inclined radially with respect to the main body around a contact position between the elastic member and the main body in the operation of the pushing shaft.

However, if the pushing shaft is inclined with respect to the main body, the front end of the pushing shaft is not precisely brought into contact with the lens placed in the main body, which may prevent the lens from being properly pushed out.

BRIEF SUMMARY OF THE INVENTION

The present invention provides an insertion device for an intraocular lens that can prevent leakage of a liquid in the device, and can house and store a lens as well as the liquid.

The present invention also provides an insertion device for an intraocular lens that can restrict the amount of leakage outside an eye of a liquid introduced into the eye through an insertion cylinder.

The present invention further provides an insertion device for an intraocular lens that can prevent inclination of a pushing shaft with respect to a main body, and can properly push out a lens.

The present invention further provides an insertion device for an intraocular lens that can facilitate introduction of liquid into the insertion device.

As one aspect, the present invention provides an insertion device for an intraocular lens that includes a main body including a lens housing portion that houses the lens and an insertion cylindrical portion that feeds the lens into an eye, a pushing shaft that moves the lens from the lens housing portion in the front end direction to push out the lens into the eye through the insertion cylindrical portion, and a lens holding member that holds the lens and is placed in the lens housing portion. The lens housing portion has a shape that receives insertion of the lens holding member from the rear.

As another aspect, the present invention provides an insertion device for an intraocular lens that includes an insertion cylinder that is inserted into an incision formed in an eyeball and feeds the lens into the eyeball, and a pushing shaft that pushes out the lens into the eyeball through the insertion cylinder. The insertion cylinder is provided with a cover portion that is brought into contact with the eyeball to cover at least part of the incision into which the insertion cylinder is inserted.

As yet another aspect, the present invention provides an insertion device for an intraocular lens that includes a main body in which the lens is placed, a pushing shaft that pushes out the lens from the main body into an eye, and a plurality of elastic members that are placed between the pushing shaft and the main body and have a distance changeable with movement of the pushing shaft relative to the main body.

As still yet another aspect, the present invention provides an insertion device for an intraocular lens that includes a main body in which the lens is placed; and a pushing shaft that pushes out the lens from the main body into an eye. The pushing shaft is constituted by a first member and a second member that are movable independently from each other in an axial direction of the device with respect to the main body.

As still further another aspect, the present invention provides the insertion device as an intraocular-lens-preloaded type insertion device.

As still further another aspect, the present invention provides a manufacturing method for the intraocular-lens-preloaded type insertion device, including the steps of preparing the insertion device and placing an intraocular lens to a lens housing portion that is formed in a main body of the insertion device.

Further objects and features of the present invention will be become more apparent from the following description of preferred embodiments with reference to the drawings.

DETAILED DESCRIPTION OF THE PREFERRED EMBODIMENTS

Exemplary embodiments of the present invention will hereinafter be described with reference to the accompanying drawings.

Figure 1A:
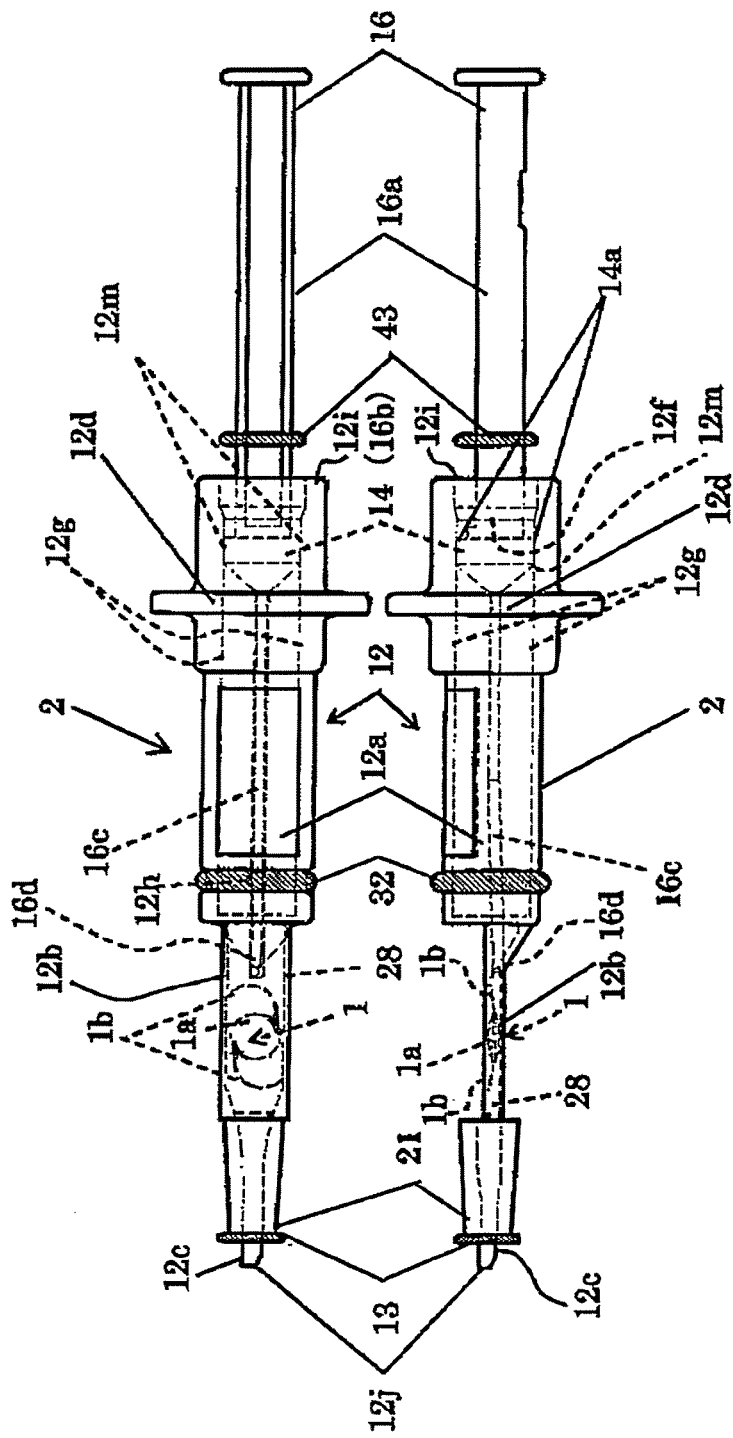
FIG. 1A is a top view and a side view of an insertion device for an intraocular lens that is an embodiment of the present invention.
Figure 2:
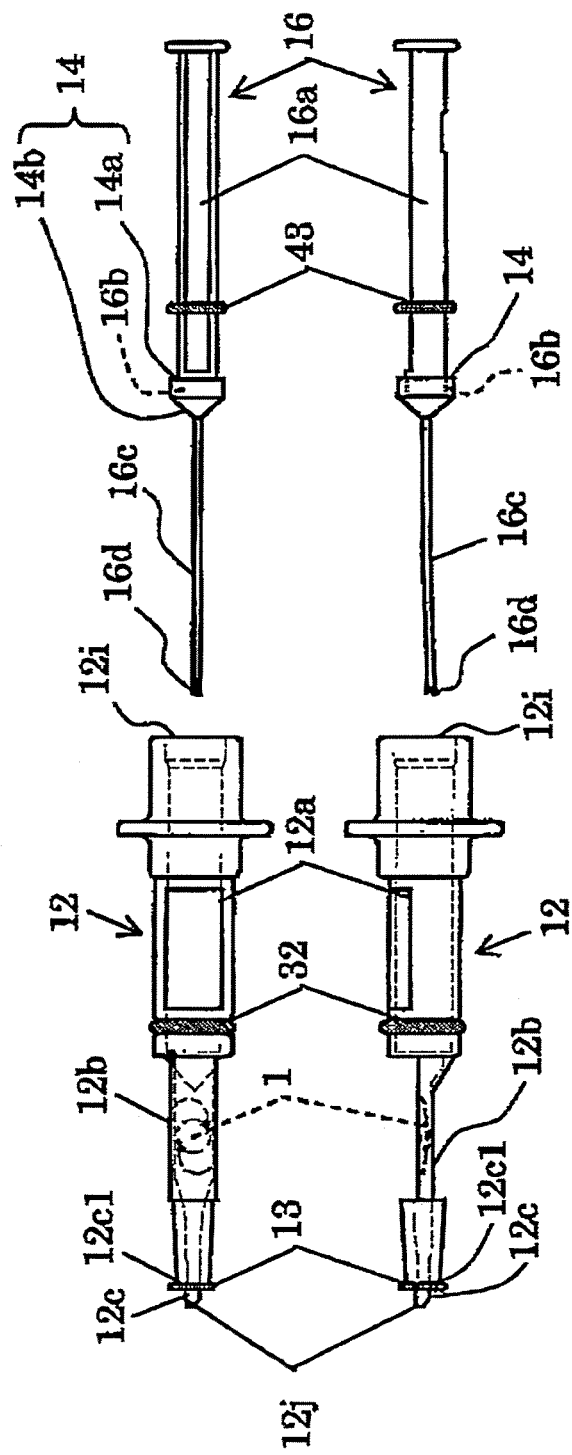
FIG. 2 is a top view and a side view before assembly of the main body with a nozzle and a pushing shaft of the embodiment.

FIG. 1A shows an insertion device for an intraocular lens (hereinafter simply referred to as a lens) that is an embodiment of the present invention. The upperside in FIG. 1A shows a top view thereof and the lowerside shows a side view thereof. FIG. 2 shows a state before a pushing shaft is assembled to a main body of the insertion device. The upperside in FIG. 2 shows a top view thereof and the lowerside shows a side view thereof.

In the description below, a nozzle side is referred to as a front end side, a front or a front end direction, and a side opposite to the nozzle side is referred to as a rear end side, a rear or a rear end direction. A direction extending toward the front end side and the rear end side is referred to as an axial direction, and a direction perpendicular to the axial direction is referred to as a vertical direction, a lateral (right-and-left) direction, or a radial direction. Further, an axis parallel to the axial direction and passing through an inner space of a main body with a nozzle or the center of a lens is referred to as a central axis, and a direction around the central axis is referred to as a circumferential direction.

An insertion device 2 is basically constituted by a main body with a nozzle (hereinafter simply referred to as a main body) 12, and a pushing shaft 16. The main body 12 includes an outer cylindrical portion 12a as a hand-held portion having an outer diameter suitable for holding the insertion device 2 by hand, a lens housing portion 12b that is provided on the side closer to the front end than the outer cylindrical portion 12a and houses a lens holding member 28 described later, and a nozzle portion 12c as an insertion cylindrical portion provided on the side closer to the front end than the lens housing portion 12b. The main body 12 is an integrally formed component (member). On the rear of the outer cylindrical portion 12a, a flange portion 12d is formed as a portion supported by hand when pushing the pushing shaft 16.

The main body 12 has a hollow shape, and the lens holding member 28 and the pushing shaft 16 are inserted through a rear end opening 12i thereof.

The outer cylindrical portion 12a has a first inner peripheral surface 12g having a cylindrical shape from the front end thereof to a position between the flange portion 12d and the rear end of the outer cylindrical portion 12a. On the side closer to the rear end than the first inner peripheral surface 12g, a second inner peripheral surface 12m having a cylindrical shape and a slightly smaller inner diameter than the first inner peripheral surface 12g is formed. Further, on the side closer to the rear end than the second inner peripheral surface 12m, a conical surface 12f is formed which has an increasing inner diameter toward the rear end. On the side closer to the rear end than the conical surface 12f, a third inner peripheral surface having a cylindrical shape and a larger inner diameter than the first inner peripheral surface 12g is formed up to the rear end opening 12i.

The nozzle portion 12c has decreasing inner and outer diameters toward the front end, and a portion from a front end opening 12j to a predetermined length is formed to be the thinnest portion in the nozzle portion 12c as a portion to be inserted into an eye through an incision formed in an eyeball. On an outer periphery of the rear end of the insertion portion, a cover ring (an O-ring) 13 made of an elastic member such as rubber is mounted. On the rear side of the cover ring 13 in the nozzle portion 12c, a step 12c1 is formed having a larger outer diameter than the insertion portion for preventing rearward movement of the cover ring 13. The function of the cover ring 13 will be described later.

The lens housing portion 12b basically has a section of a hollow flat plate shape having a vertical dimension smaller than a lateral dimension in axial view. A rear portion in a lower surface of the lens housing portion 12b near a boundary with the outer cylindrical portion 12a has a semi-conical shape having an increasing diameter toward the rear for reinforcement. The lens housing portion 12b is inserted through the rear end opening 12i, and thus a connection between the outer cylindrical portion 12a and an inner surface of the lens housing portion 12b is tapered to provide a guide configuration and facilitate insertion when the holding member 28 is inserted.

The lens housing portion 12b can receive the insertion of the lens holding member 28 from the rear end thereof, and has an inner surface shape that can stably hold the inserted lens holding member 28.

Figure 1B:
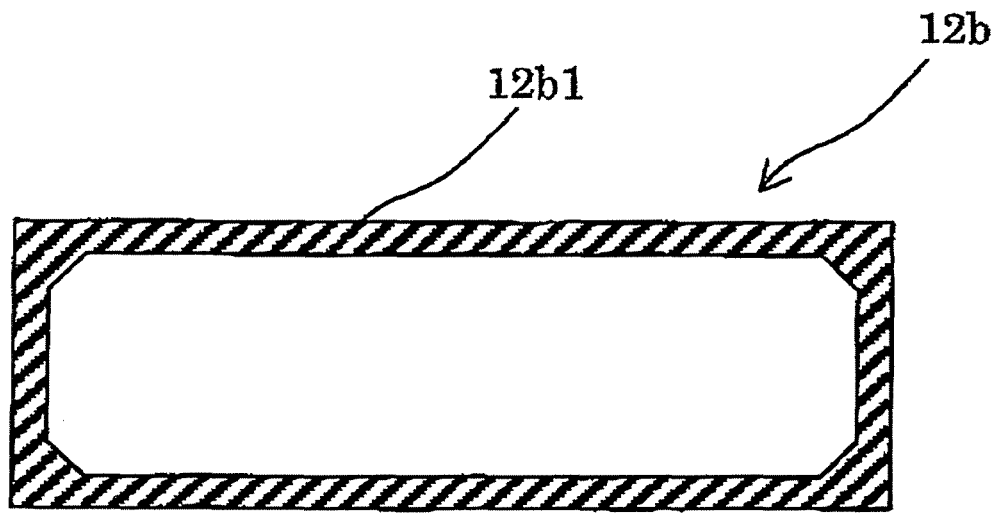
FIG. 1B is a sectional view of a lens housing portion in a main body with a nozzle of the embodiment.
Figure 1C:
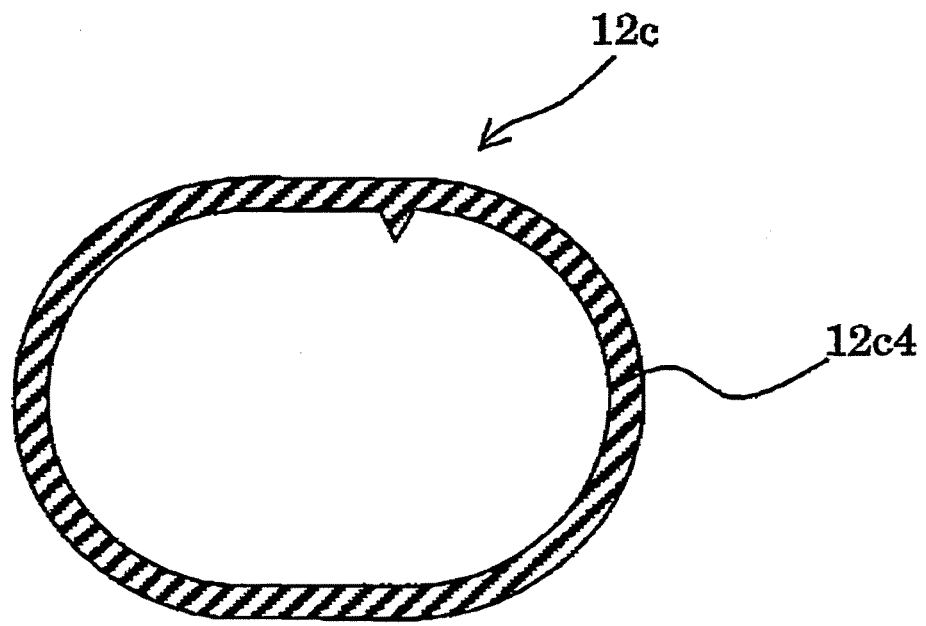
FIG. 1C is a sectional view of a nozzle portion in the main body with a nozzle of the embodiment.

As shown in FIGS. 1B and 1C showing sections perpendicular to an axis of the lens housing portion 12b and the nozzle portion 12c, respectively, peripheral walls 12b1 and 12c4 from the lens housing portion 12b to the nozzle portion 12c are formed as integral walls without an opening and a gap. In other words, four side (upper, lower, right and left) walls surrounding an inner space are circumferentially connected, and integrally formed without an opening such as a hole and a dividable portion or an openable and closable portion in which a gap is created in an assembled portion.

In the embodiment, the case is described where the main body 12 is produced as an integrally formed component (member) so that at least the peripheral walls 12b1 and 12c4 from the lens housing portion 12b to the nozzle portion 12c have no opening or gap. However, an alternative embodiment of the present invention is not limited to this case. For example, it is allowed that components divided into two upper and lower portions from the front end to the rear end may be joined by thermal welding or bonding and integrated to constitute the main body 12, and the main body 12 is thereby made as an integral component (member) without a gap at least in peripheral walls of the lens housing portion 12b and nozzle portion 12c after completion of the main body 12 (before insertion of the lens holding member 28). It is also allowed that the lens housing portion 12b, the nozzle portion 12c and the outer cylindrical portion 12a that are formed in a divided manner are joined by thermal welding or bonding, and the main body 12 is thereby made as an integral component without a gap at least in peripheral walls from the lens housing portion 12b to the nozzle portion 12c after completion of the main body 12 (before insertion of the lens holding member 28).

As shown by a dotted line in the top view in FIG. 1A, a small hole 12h is formed in a peripheral wall near the front end of the outer cylindrical portion 12a. This hole 12h is naturally formed for placing a member that supports a die for forming the inner surface of the main body 12 in production of the main body 12, that is, when the main body 12 is integrally formed of resin.

In the embodiment, in order to completely cover the hole 12h, an O-ring 32 made of an elastic member such as rubber is mounted to the outer periphery of the outer cylindrical portion 12a. Thus, the main body 12 has no opening other than the rear end opening 12i in the outer cylindrical portion 12a and the front end opening 12j in the nozzle portion 12c. Thus, as described later, the rear end opening 12i is covered with a seal cap 14 provided on the pushing shaft 16 without a gap, and the front end opening 12j is covered with a cap 34 described later without a gap, thereby allowing a sealed space to be formed in the main body that can house a liquid such as a viscoelastic material or physiologic saline without leakage, and store the liquid with the lens 1.

A mounting surface for the O-ring 32 on the outer peripheral surface of the outer cylindrical portion 12a has a diameter smaller than those on the sides closer to the front and rear ends. This prevents axial movement of the O-ring 32 on the outer cylindrical portion 12a. The O-ring 32 is provided on a position often touched by hand of an operator holding the insertion device 2. Thus, the O-ring 32 has the function of covering the hole 12h as well as the function of preventing slip of the hand holding the Insertion device 2. If not covering the hole 12h does not directly influence the flow of the liquid, covering of the hole 12h is not necessarily required.

The lens holding member 28 includes a first holding member 28A that supports the lens 1 from below, and a second holding member 28B that retains from above the lens 1 in combination with the first holding member 28A.

First, the configuration of the lens 1 held by the lens holding portion will be described. The lens 1 has a circular shape in top view, and includes an optical portion 1a having the function of a lens and support portions 1b extending from the front end and the rear end of the optical portion 1a.

The support portion 1b is a wire-like portion that elastically supports the optical portion 1a in the eye after the lens 1 is inserted into the eye.

A ring-shaped marginal (peripheral) portion 1c having parallel upper and lower surfaces is formed around the optical portion 1a. The marginal portion 1c is hereinafter referred to as the lens marginal portion 1c.

As shown in FIG. 3A, the first holding member 28A is formed laterally symmetrically with respect to the central axis CA passing through the center O of the optical portion 1*a* of the lens 1 except part thereof. Support surfaces 28*a* are formed on the right and left in the lower portion of the first holding member 28A. The support surfaces 28*a* are formed as inclined surfaces whose inner portion is lower than its outer portion in the lateral direction.

Figure 3:
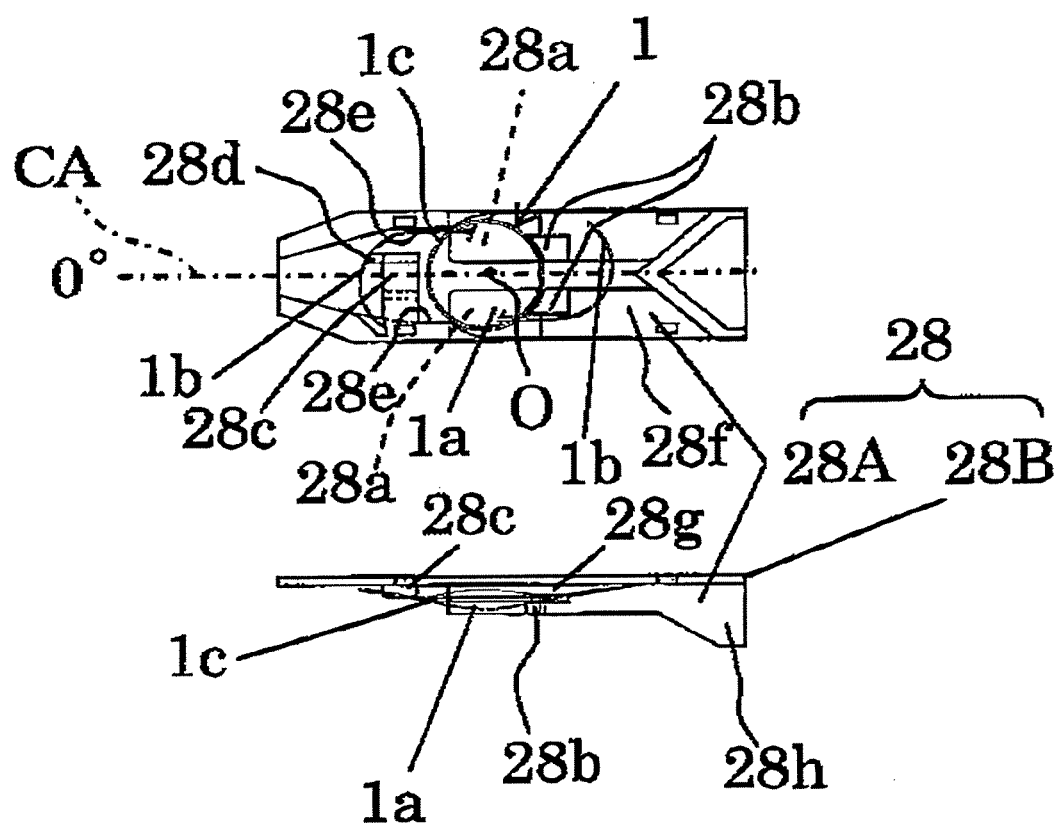
FIG. 3 is a top view and a side view of a lens holding member of the embodiment.

In a top view in FIG. 3, a position in the front end direction from the center O of the optical portion 1*a* in the lens marginal portion 1*c* (a position on the central axis CA) is a 0° position. The right and left support surfaces 28*a* contact arcuate regions between positions retracted by a circumferential angle of 60° to both circumferential sides (60° positions, other positions are hereinafter referred to as the same) from the 0° position in the lens marginal portion 1*c*, and 90° positions retracted by a circumferential angle of 90°, and support the arcuate regions from below.

On the right and left in the axial middle of the first holding member 28A, support protrusions 28*b* are formed which support arcuate regions between 135° positions to 165° positions which are regions closer to the rear than the arcuate regions supported by the support surfaces 28*a* in the lens marginal portion 1*c*. A space through which the pushing shaft 16 (a pushing shaft portion 16*c*) passes is provided between the support protrusions 28*b*. Since the space has only a 30° angle range, it may be considered that the support protrusions 28*b* support an arcuate region of a 90° angle range around a 180° position in the lens marginal portion 1*c*. Specifically, the first lens support member 28A supports the lens marginal portion 1*c* at three points at 120° intervals including the right and left 60° positions and the 180° position.

Each of the support protrusions 28*b* has a horizontal surface on which the lens marginal portion 1*c* is placed and a vertical surface that contacts or is brought close to an outer peripheral end surface of the lens marginal portion 1*c* on the rear side of the horizontal surface, supports the lens marginal portion 1*c* from below, and prevents rearward movement of the lens 1.

Further, on the right and left on the front end side of the first holding member 28A, a vertical surface 28*e* is formed that contacts or is brought close to the 60° position in the outer peripheral end surface of the lens marginal portion 1*c*. The vertical surface 28*e* prevents movement of the optical portion 1*a* in the front end direction in a state before pushing out the lens 1.

In an upper portion at the front end of the first holding member 28A, an arm 28*c* is formed extending from one side to the other side in the lateral direction (from the lower side to the upper side in the top view in FIG. 3), and at the tip of the arm 28*c*, a protrusion 28*d* that supports from below the front side support portion 1*b* is formed to extend in the front end direction.

On the rear of the first holding member 28A, an inclined surface 28*f* that supports from below the rear side support portion 1*b* is formed so that its portion closer to the rear end is placed in a higher position.

Next, the configuration of the second holding member 28B will be described. The second holding member 28B is placed above the first holding member 28A. The first and second holding members 28A and 28B are inserted into the lens housing portion 12*b* while holding the lens 1, and held between a ceiling surface and a bottom surface of the lens housing portion 12*b* without displacement.

The second holding member 28B is formed laterally symmetrically with respect to the central axis CA, though not shown. On the right and left in a lower surface of the second holding member 28B, retaining protrusions 28*g* are formed that contact or are brought close to arcuate regions from the 90° positions to 120° positions and arcuate regions from the 135° positions to the 165° positions on the right and left in the lens marginal portion 1*c*. A space through which the pushing shaft 16 (the pushing shaft portion 16*c*) passes is provided between the right and left retaining protrusions 28*g* with the 180° position therebetween.

A portion on the front side of the retaining protrusion 28*g* retains from above an arcuate region closer to the rear than the arcuate region that contacts the support surface 28*a* provided in the first holding member 28A in the lens marginal portion 1*c*, and a portion on the rear side of the retaining protrusion 28*g* retains from above the arcuate region supported from below by the support protrusion 28*b* provided in the first holding member 28A in the lens marginal portion 1*c*.

As shown in a side view in FIG. 3, the second holding member 28B is assembled to the upper side of the first holding member 28A, and thus the arcuate regions from the 60° positions to the 90° positions in the lens marginal portion 1*c* are supported from below by the support surfaces 28*a* of the first holding member 28A, and the arcuate regions from the 90° positions to the 120° positions are retained from above by the front side portions of the retaining protrusions 28*g* in the second holding member 28B. The arcuate regions from the 135° positions to the 165° positions are vertically held by the horizontal surfaces of the support protrusions 28*b* provided In the first holding member 28A and the rear side portions of the retaining protrusions 28*g* provided in the second holding member 28B therebetween. With such a holding structure, the lens 1 is supported in a state in which the optical portion 1*a* of the lens 1 is held in a horizontal state and a stress by its own weight or an external force is not substantially applied.

The state in which a stress is not substantially applied denotes a state in which no stress is applied to the optical portion at all as well as a state in which a minute stress is applied so that a deformation influencing the optical function of the optical portion 1*a* after insertion of the lens 1 into the eye does not occur even if the lens 1 is held and stored for a long time. In other words, the state denotes a state in which a stress or a deformation influencing the optical function of the optical portion 1*a* does not occur.

The vertical surfaces 28*e* that contact the 60° positions in the outer peripheral end surface of the lens marginal portion 1*c* and the vertical surfaces of the support protrusions 28*b* that contact the regions from the 135° positions to the 165° positions prevent displacement of the lens 1 in the front end direction and the rear end direction. Further, the front end side of the lens marginal portion 1*c* is opened by 120° by providing the right and left vertical surfaces 28*e* in the 60° positions. This allows the lens 1 to be smoothly moved from the lens holding member 28 in the front end direction in pushing out the lens 1.

On the side closer to the rear than the portions retaining the lens marginal portion 1*c* of the retaining protrusions 28*g* in the second holding member 28B, inclined portions are formed that extend in parallel with the inclined surface 28*f* in the first holding member 28A and hold the rear side support portion 1*b* together with the inclined surface 28*f*.

Further, the vertical surfaces 28*e* in the first holding member 28A are formed such that one of them extends in the front end direction along the outer edge of the front side support portion 1*b* and the other extends in the same shape as the one. The contact of the one of the vertical surfaces 28*e* with the front side support portion 1*b* and the holding of the rear side support portion 1*b* between the inclined surface 28*f* and the inclined portions of the retaining protrusions 28*g* prevent rotation of the lens 1.

In an alternative embodiment of the present invention, the configuration of the lens holding member is not limited to the above case, and any lens holding member may be allowed that can hold a lens in a state in which a stress is not substantially applied to an optical portion. The lens is not limited to one having an optical portion and a wire-like support portion, but may have an optical portion and a support portion having a flat plate shape.

Figure 20:
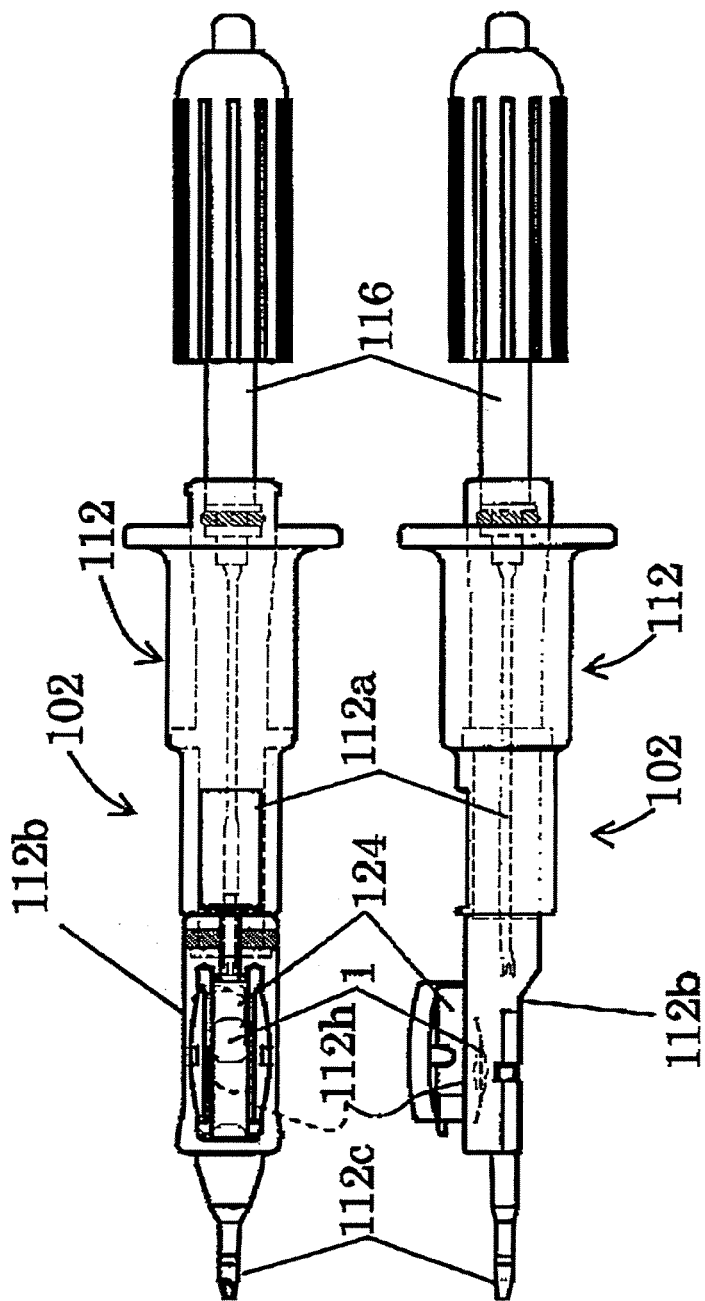
FIG. 20 is a top view and a side view of a conventional type insertion device.

FIG. 20 shows a conventional type insertion device. The upperside in FIG. 20 shows a top view thereof and the lowerside shows a side view thereof. A main body 112 of the insertion device 102 is constituted by a plurality of components including an outer cylinder 112a, a lens holding member 112b assembled to the front end of the outer cylinder 112a, and a nozzle 112c assembled to the lens holding member 112b so as to extend from a lower surface of the lens holding member 112b to the front end. An opening 112h is formed in an upper surface of the lens holding member 112b, and a lens 1 is set in the lens holding member 112b through the opening 112h. A cover member 124 is mounted to the lens holding member 112b so as to cover the opening 112h.

In this conventional type insertion device 102, gaps are created at assembled portions of the plurality of components. In the lens holding member 112b corresponding to the lens housing portion 12b of the embodiment, the opening 112h through which the lens 1 is set is formed, and a gap leading to the outside from the opening 112h is created even if the opening 112h is covered with the cover member 124.

Thus, when a liquid such as a viscoelastic material or physiologic saline is introduced into the main body 112, the liquid leaks from the gap. Particularly, physiologic saline having a lower viscosity than the viscoelastic material leaks immediately after being introduced, and it is difficult to maintain the viscoelastic material in an amount required for an operation in the main body 112. Though the amount of leakage of the viscoelastic material is small because of its viscosity, the leakage may make the insertion device 102 slippery and is unpreferable.

As shown in FIGS. 1A and 2, the pushing shaft 16 has a D-cut shaft portion 16a, a cylindrical portion 16b, and a pushing shaft portion 16c in order from the rear end side thereof. The D-cut shaft portion 16a has a so-called D-cut shape having a section in axial view of a non-rotationally symmetric shape with a circular upper portion cut to be flat. On the D-cut shaft portion 16a, an O-ring (a second elastic member) 43 made of an elastic member such as rubber is mounted axially movably relative to the D-cut shaft portion 16a.

The cylindrical portion 16b has the same or a smaller outer diameter as or than a cylindrical portion of the D-cut shaft portion 16a, and the seal cap (a first elastic member) 14 made of an elastic member such as rubber is mounted to the outer periphery of the cylindrical portion 16b. The seal cap 14 has a ring portion 14a mounted on the cylindrical portion 16b, and a conical portion 14b having a decreasing diameter from the front end of the ring portion 14a toward the front end. A hole through which the pushing shaft portion 16c passes is formed in the front end of the conical portion 14b.

The pushing shaft portion 16c has a small outer diameter that can pass through an inner passage of the nozzle portion 12c, and has, at the front end thereof, a lens grip portion (lens contact portion) 16d vertically bifurcated. The lens grip portion 16d vertically holds the rear end of the optical portion 1a of the lens 1 held by the lens holding member 28 in the lens housing portion 12b. This allows the lens 1 to be reliably pushed by the pushing shaft 16 in the front end direction.

In the conventional type insertion device such as the insertion device in FIG. 20, a rubber ring is mounted on an outer periphery of a pushing shaft, and the rubber ring slides relative to an inner surface of the main body with movement of the pushing shaft. However, the rubber ring is intended for providing proper sliding feeling (operation resistance) to an operation of the pushing shaft, and has no sealing function of preventing leakage of a liquid housed in the main body.

On the other hand, the seal cap 14 of the embodiment mainly has the sealing function, and is brought into press contact with the inner peripheral surface of the main body 12 by a press-contact force for achieving the sealing function, thereby also providing sliding feeling.

In the embodiment, in order to achieve the sealing function, an axial width of the ring portion 14a of the seal cap 14 is set to 2 mm or more, and further, on the front end side of the ring portion 14a, the conical portion 14b is provided for preventing the liquid from leaking from the gap between the ring portion 14a and the cylindrical portion 16b of the pushing shaft 16. Further, in the embodiment, in a state before pushing of the pushing shaft 16 (an assembly completion state or a storage state) in FIG. 1A, the inner diameter of the second inner peripheral surface 12m with which the ring portion 14a of the seal cap 14 is brought into press contact in the inner peripheral surface of the main body 12 is set to be smaller than the inner diameter of the first inner peripheral surface 12g formed on the side closer to the front end than the second inner peripheral surface 12m. The inner diameter of the second inner peripheral surface 12m is set to be small to increase the press-contact force with the ring portion 14a of the seal cap 14, thereby increasing the sealing function. Specifically, as described later, the insertion device 2 can be stored so that the liquid introduced into the main body 12 does not leak. The inner peripheral surfaces 12g and 12m of the main body are preferably circular.

The outer peripheral surface of the ring portion 14a of the seal cap 14 may be a simple cylindrical surface, but in order to increase the sealing function, the outer peripheral surface may have a ring shape with a semicircular section or have a plurality of ring shapes in the axial direction.

As described above, the lens grip portion 16d that holds the upper and lower surfaces of the optical portion 1a of the lens 1 is provided in the front end of the pushing shaft 16, and when the pushing shaft 16 is pushed in a state in which the pushing shaft 16 is rotated with respect to the main body 12, the lens grip portion 16d cannot properly push the optical portion 1a. Thus, particularly before pushing of the pushing shaft 16, the rotation of the pushing shaft 16 with respect to the main body 12 needs to be prevented. Further, if the pushing shaft 16 is removed from the main body 12 before pushing or after the start of the pushing, reinsertion thereafter of the pushing shaft 16 into the main body 12 is not always properly performed, and thus the removal needs to be prevented. In these views, the function required for the pushing shaft 16 of the insertion device 2 is different from a simple sealing function required for a general syringe.

Thus, in the embodiment, as described above, the inner diameter of the second inner peripheral surface 12m is set to be small, and using an increase thereby in the press-contact force between the ring portion 14a of the seal cap 14 and the second inner peripheral surface 12m, that is, a friction force, the configuration is achieved in which the pushing shaft 16 is hardly rotated with respect to the main body 12 or removed from the main body 12.

In the embodiment, the case has been described where the rotation of the pushing shaft 16 with respect to the main body 12 or the removal thereof from the main body 12 is restricted using friction caused by press contact between the seal cap 14 and the main body 12, but the rotation or the removal of the pushing shaft may be restricted by other methods. For example, it is possible that the main body 12 has an inner peripheral shape similar to an outer peripheral shape of the D-cut shaft portion 16a of the pushing shaft 16, and flat surface portions thereof contact each other to prevent rotation of the pushing shaft 16 with respect to the main body 12. A step formed between the D-cut shaft portion 16a and the cylindrical portion 16b (the seal cap 14) may contact a contact surface formed in the main body 12 to prevent removal of the pushing shaft 16 from the main body 12.

Figure 21:
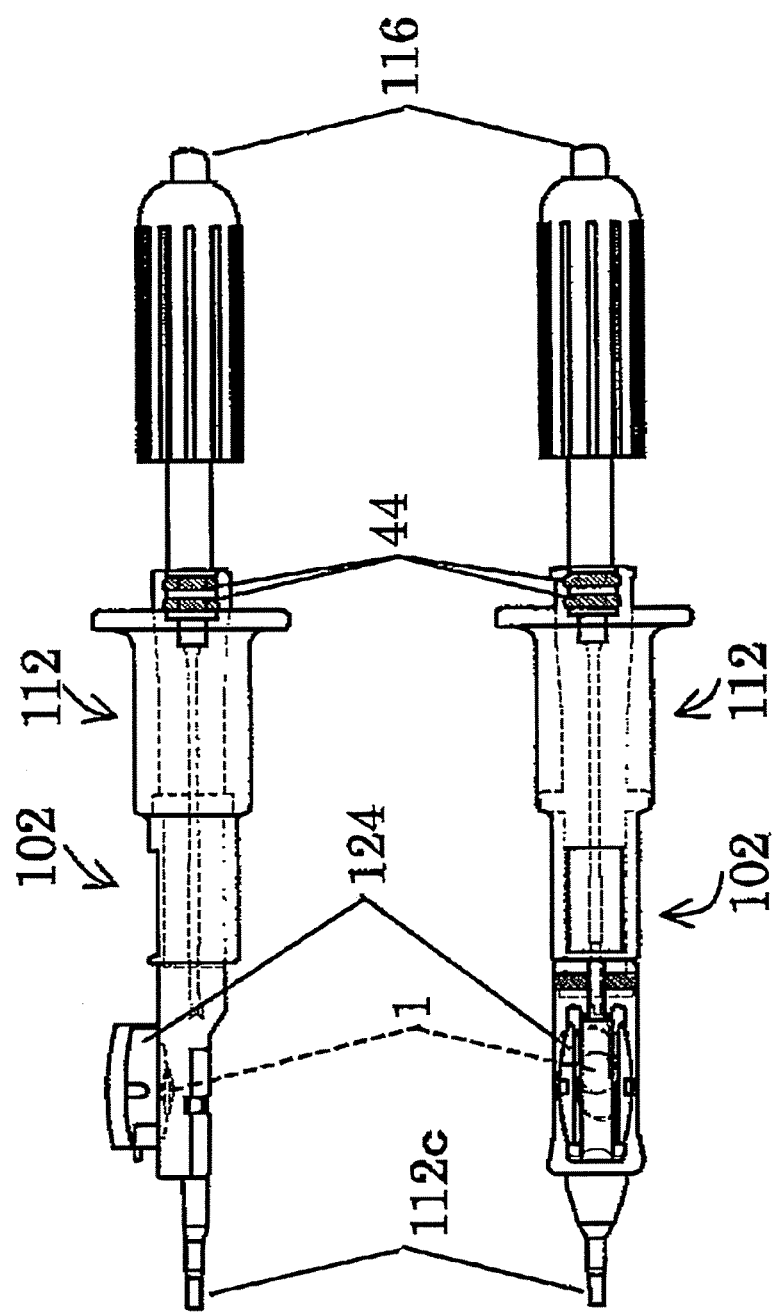
FIG. 21 is a side view and a top view of an insertion device (of a conventional type) of an embodiment.

The relationship between the seal cap 14 and the inner peripheral surface of the main body 12 in the embodiment may be applied to the conventional type insertion device as shown in FIG. 21. FIG. 21 (the upperside shows a side view and the lowerside shows a top view) shows the configuration in which a double seal ring 44 corresponding to the seal cap 14 in the embodiment is provided in the pushing shaft 116, and the inner diameter of a portion (seal portion) with which the double seal ring 44 is brought into press contact in the inner peripheral surface of the rear end side portion of the main body 112 is smaller than that of an inner peripheral surface of a portion closer to the front end than the above seal portion.

Figure 4:
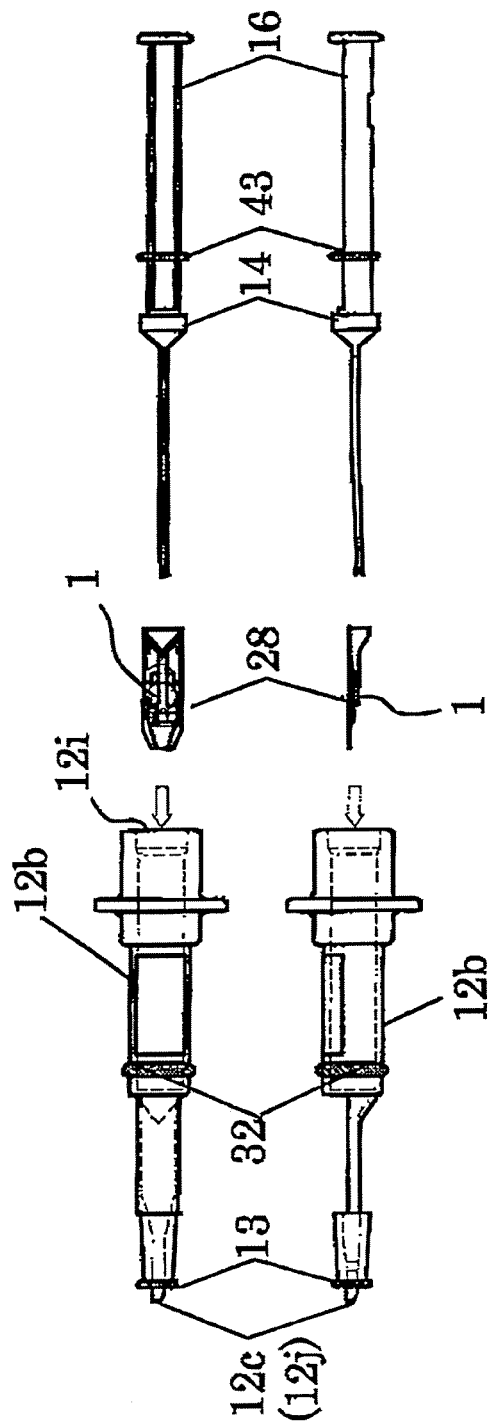
FIG. 4 is a top view and a side view showing an assembling procedure of the insertion device of the embodiment.

An assembling procedure of the insertion device 2 thus configured will be described with reference to FIG. 4 (the upperside shows a top view and the lowerside shows a side view). First, the lens 1 is held by the lens holding member 28. Then, the O-ring and the cover ring 13 are mounted to the outer peripheries of the outer cylindrical portion 12a and the nozzle portion 12c, respectively, of the main body 12. When the hole 12h is used for introducing a liquid into the main body 12 after the assembly, it is recommended to displace the O-ring 32 to a position where it does not cover the hole 12h.

Then, the lens holding member 28 is inserted from the rear into the lens housing portion 12b through the rear end opening 12i. The lens holding member 28 inserted into the lens housing portion 12b is held by contact of the outer surface thereof with the inner surface of the lens housing portion 12b substantially without circumferential and axial backlash.

Next, the pushing shaft 16 to which the O-ring 43 and the seal cap 14 are mounted is inserted into the main body 12 through the rear end opening 12i. The pushing shaft 16 is inserted until the lens grip portion 16d reaches the immediate rear of the lens 1 in the lens housing portion 12b. At this time, the outer peripheral surface of the ring portion 14a of the seal cap 14 is brought into press contact with the second inner peripheral surface 12m of the outer cylindrical portion 12a to perform the sealing function and the rotation and removal preventing function described above.

The O-ring 43 is also caused to contact the conical surface 12f formed in the inner periphery of the outer cylindrical portion 12a. The function of the O-ring 43 will be described later.

Into the insertion device 2 assembled as described above, a liquid is introduced such as a viscoelastic material such as sodium hyaluronate or physiologic saline (including one in which drug is dissolved) as described later. A liquid introduction method will be described below. A liquid to be introduced includes hydrophilic (water-soluble) polymer liquid besides sodium hyaluronate or physiologic saline. For example, synthetic polymer includes polyethylene glycol (PEG), polypropylene glycol (PPG), sodium polyacrylate (PAA), polyacrylamide (PAAm), sodium polystyrene sulfonate (PSSNa), polyvinylpyrrolidone (PVP), polyvinyl alcohol (PVA), polyethyleneimine (PEI), carboxymethylcellulose (CMC), dextran sodium sulfate, hydroxyethyl starch (HEPES), and polyphosphoric acid.

Natural polymer includes hyaluronate and/or sodium hyaluronate (HA), sodium alginate, dextran, dextrin, heparin, chitosan, and sodium chondroitin sulfate as polysaccharide, and polypeptide and polynucleic acid as other than polysaccharide.

Among them, polysaccharide is preferably used in view of biocompatibility or the diversity of molecular weight obtained.

Next, several methods of introducing a liquid such as physiologic saline having a lower viscosity than the viscoelastic material into the main body 12 will be described.

Figure 5:
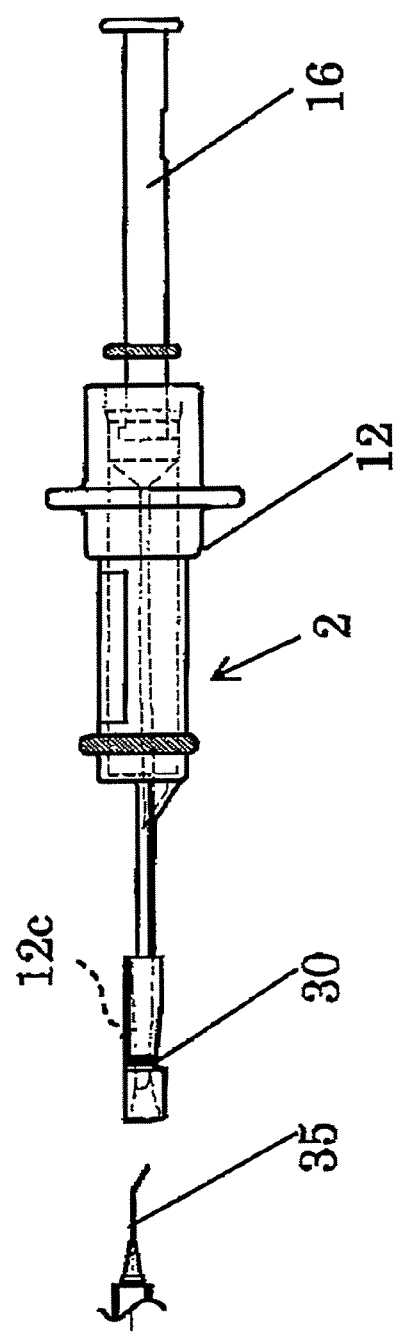
FIG. 5 is a side view for illustrating a liquid introduction method into the insertion device of the embodiment.

FIG. 5 shows a first liquid introduction method. The liquid in a syringe 35 is introduced through an injection needle inserted into the front end opening 12j of the nozzle portion 12c. At this time, it is recommended to mount to the nozzle portion 12c a guide member 30 that guides the injection needle to the front end opening 12j so as to facilitate insertion of the injection needle into the front end opening 12j. At this time, the O-ring 32 is placed to cover the hole 12h formed in the main body 12.

The liquid introduced into the main body 12 hardly leaks even if the front end opening 12j is directed downward because the main body 12 has no opening leading to the outside other than the front end opening 12j. This also applies to liquid introduction methods described below.

Figure 6A:
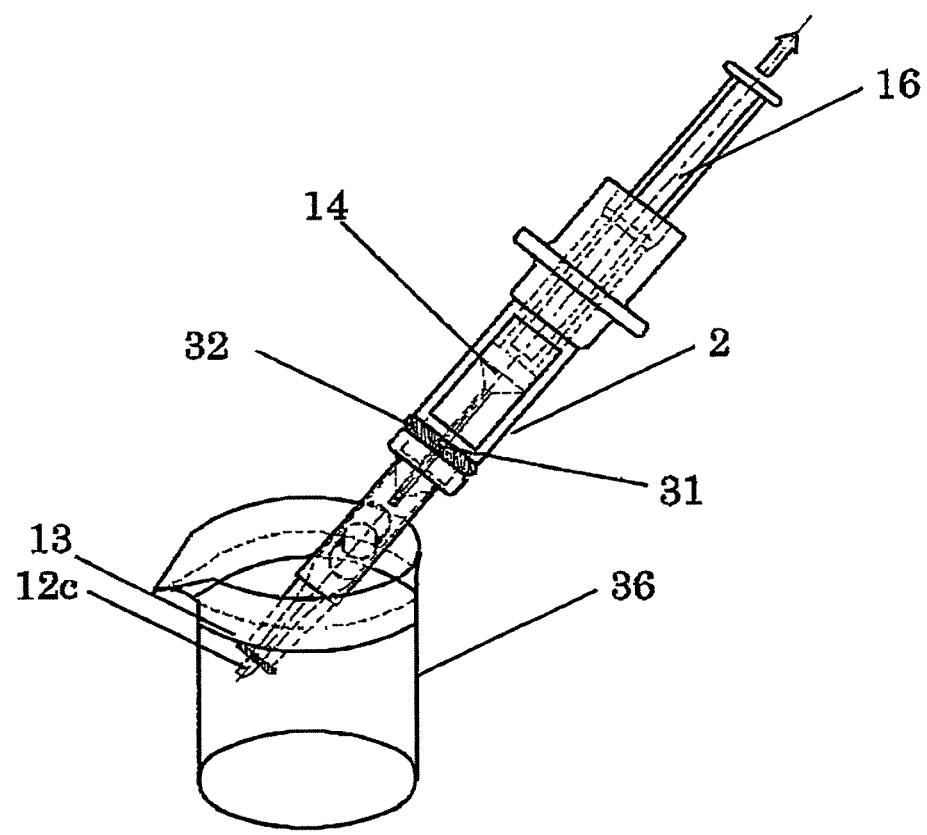
FIG. 6A is a perspective view for illustrating the liquid introduction method into the insertion device of the embodiment.

FIG. 6A shows a second liquid introduction method. The liquid is placed in a container 36 such as a sterile beaker, and the pushing shaft 16 is drawn rearward in a state in which the nozzle portion 12c is inserted in the liquid. The main body 12 is sealed except the front end opening 12j, thereby allowing the liquid to be introduced (filled) into the main body 12 similarly to the syringe 35.

However, when the pushing shaft 16 is a single-shaft type that is integrally formed and has the lens grip portion 16d, it is necessary that the pushing shaft 16 be drawn rearward from a state in which the lens grip portion 16d is located slightly rearward of the optical portion 1a of the lens 1 in the lens housing portion 12b. Therefore, the length by which the pushing shaft 16 can be drawn rearward is short, thereby making it difficult to introduce a sufficient amount of the liquid into the main body 12.

Figure 6B:
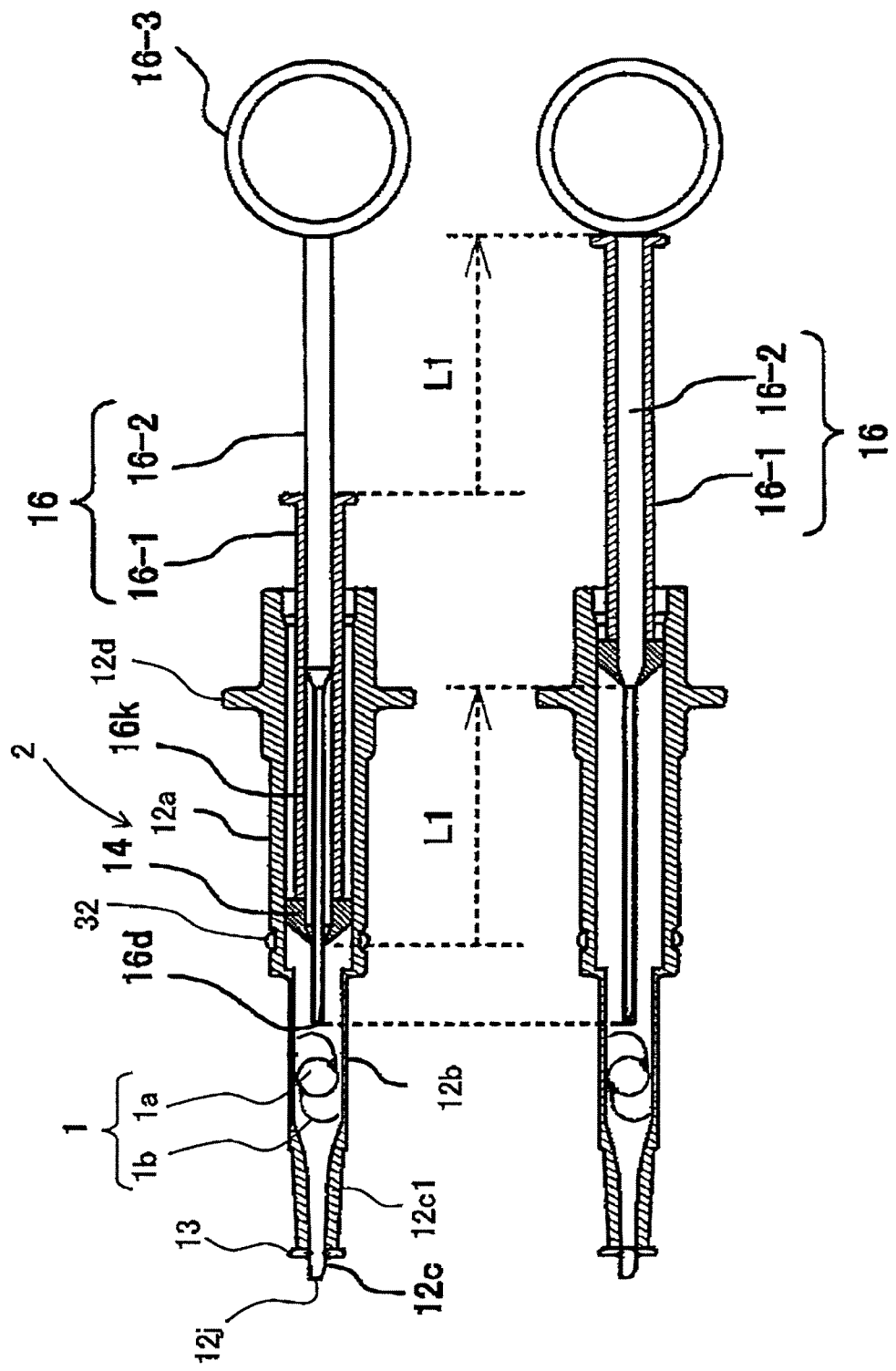
FIG. 6B is a sectional view of the insertion device of the embodiment having the pushing shaft of a two-shaft configuration.

Thus, in order to introduce a sufficient amount of the liquid into the main body 12 by a similar operation to that for the syringe 35, it is preferable that a two-shaft configuration is employed as shown FIG. 6B.

Specifically, a through hole (opening) 16k is formed in an outer shaft member (second member) 16-1 with the seal cap 14 mounted at the tip thereof, the through hole 16k extending in the axial direction of the outer shaft member 16-1. Then, a pushing member (first member) 16-2 having the lens grip portion 16d at the tip thereof is inserted into the through hole 16k to be assembled to the outer shaft member 16-1. The outer shaft member 16-1 and the pushing member 16-2 are concentrically assembled as shown in FIG. 6G. The pushing member 16-2 is held so as to be movable in the axial direction by the outer shaft member 16-1. The outer shaft member 16-1 is a member having no function of pushing the lens 1, which is different from the pushing member 16-2 having the lens grip portion 16d, that is, a function of pushing the lens 1.

The inner surface of the outer shaft member 16-1 is in close contact with the outer surface of the pushing member 16-2, which prevents leakage of the liquid through therebetween. The pushing member 16-2 and the outer shaft member 16-1 are movable independently from each other in the axial direction with respect to the main body 12. In other words, it is possible to move with respect to the main body 12 only the pushing member 16-2, only the outer shaft member 16-1, or both the members 16-1 and 16-2.

The upper figure of FIG. 6B shows a state in which the pushing member 16-2 is set such that the lens grip portion 16*d* is located slightly rearward of the lens 1 and the outer shaft member 16-1 is inserted up to the vicinity of the mounted position of the O-ring 32 in the main body 12. The lower figure of FIG. 6B shows a state in which the pushing member 16-2 is set at the same position as that shown in the upper figure of FIG. 6B and the outer shaft member 16-1 is moved rearward from the position shown in the upper figure.

Figure 6C:
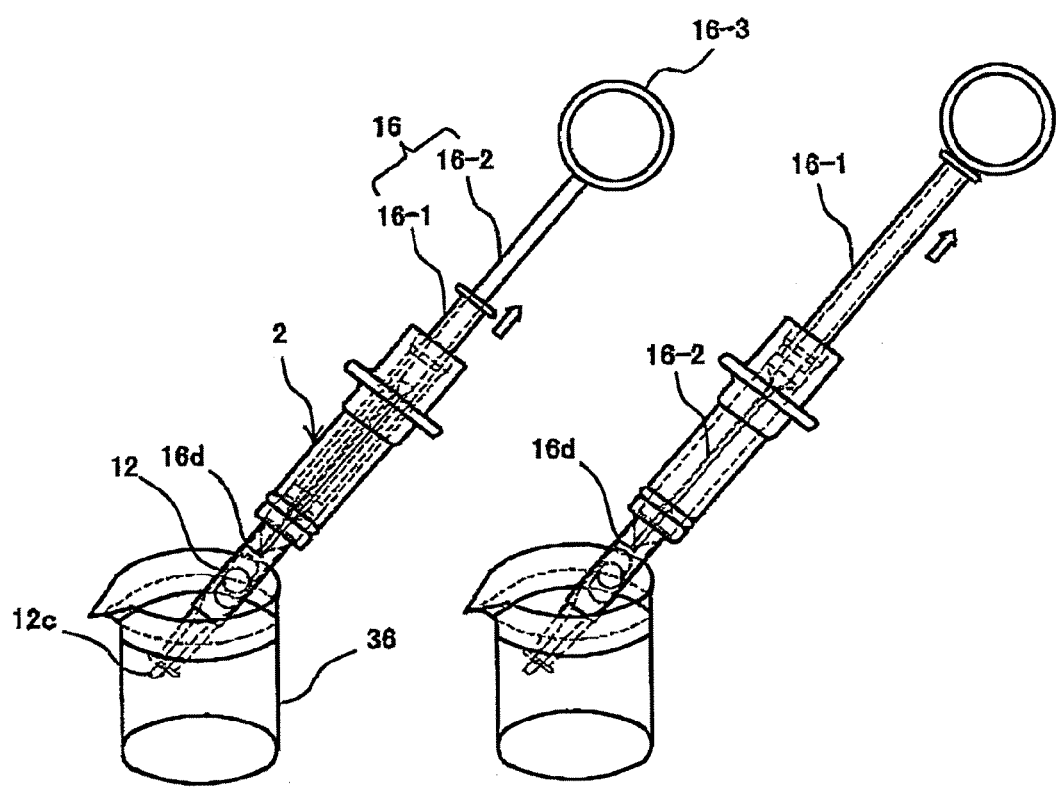
FIG. 6C is a perspective view for illustrating a liquid introduction method into the insertion device shown in FIG. 6B.
Figure 6D:
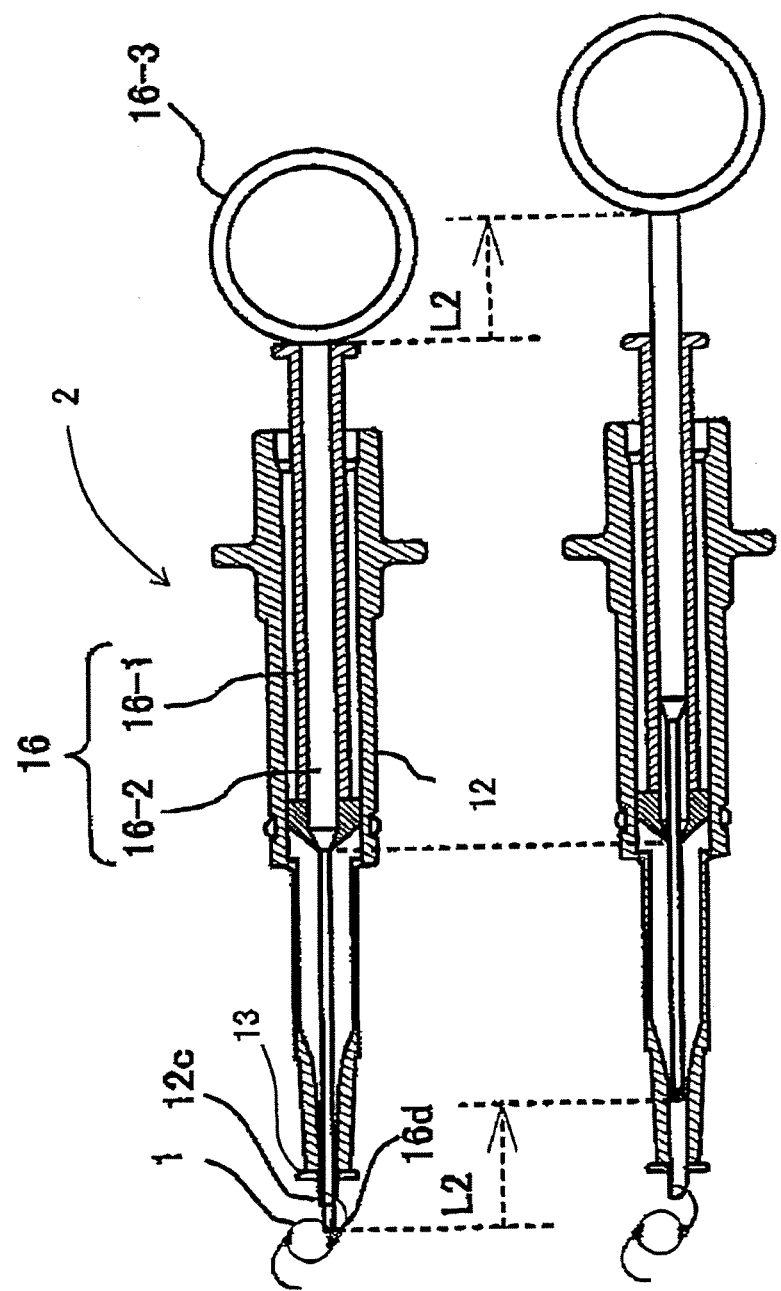
FIG. 6D is a sectional view for illustrating an operation of the insertion device shown in FIG. 6B.
Figure 6E:
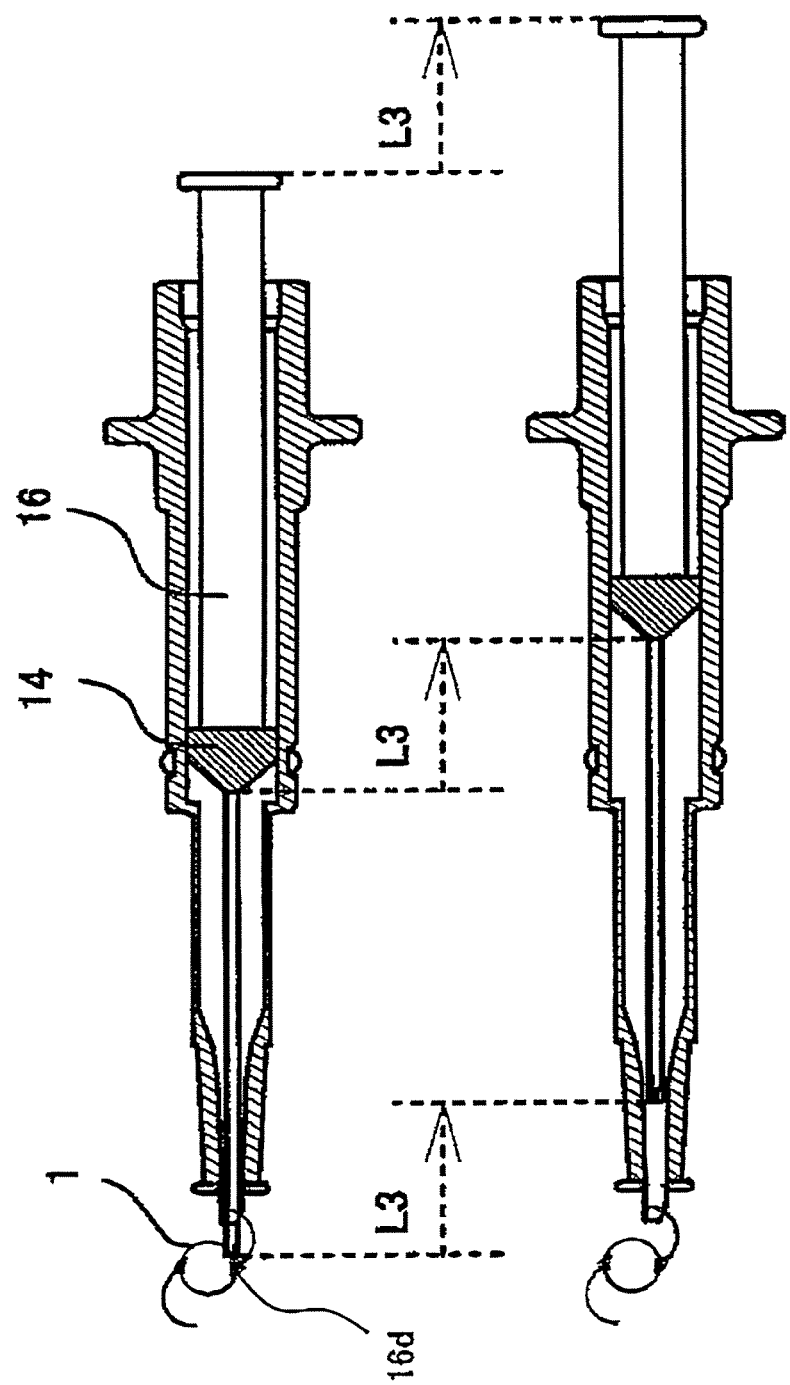
FIG. 6E is a sectional view of the insertion device having the pushing shaft of a one-shaft configuration.

When the liquid is introduced into the insertion device 2 having the pushing shaft 16 of such a two-shaft configuration, as shown in FIG. 6C, the nozzle portion 12*c* of the insertion device 2 being in the state shown in the upper figure of FIG. 6B is inserted in the liquid in the container (beaker) 36 and then the outer shaft member 16-1 is drawn rearward with the pushing member 16-2 fixed. This enables the seal cap 14, as shown in the lower figure of FIG. 65, to move rearward with the lens grip portion 16*d* of the pushing member 16-2 located slightly rearward of the lens 1. This allows the liquid to be introduced (filled) into the main body 12 similarly to the syringe.

In an operation (surgery), an operation ring (interlocking portion) 16-3 provided at the rear end of the pushing member 16-2 is held by a hand to push the pushing member 16-2 frontward from the state shown in the lower figure of FIG. 6B (the right figure of FIG. 6C). The operation ring 16-3 is thereby brought into contact with the rear end of the outer shaft member 16-1, as shown in the upper figure of FIG. 6D, to move the outer shaft member 16-1 frontward together with the pushing member 16-2. Thereby, the lens 1 is pushed out through the nozzle portion 12*c* by the lens grip portion 16*d* of the pushing member 16-2 to be inserted into the eye, and the liquid filled in the main body 12 is flowed into the eye by the forward movement of the seal cap 14.

Figure 6F:
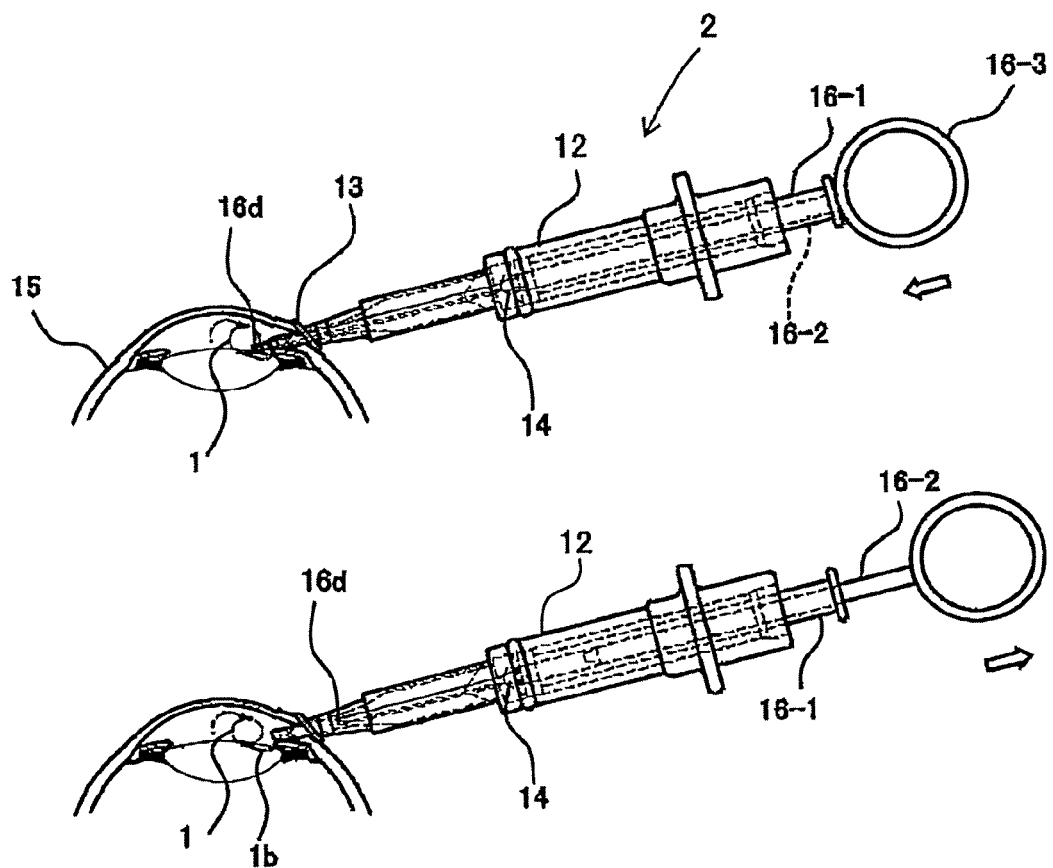
FIG. 6F is a figure for illustrating an operation method of the insertion device shown in FIG. 6B in an operation of the eye.
Figure 6G:
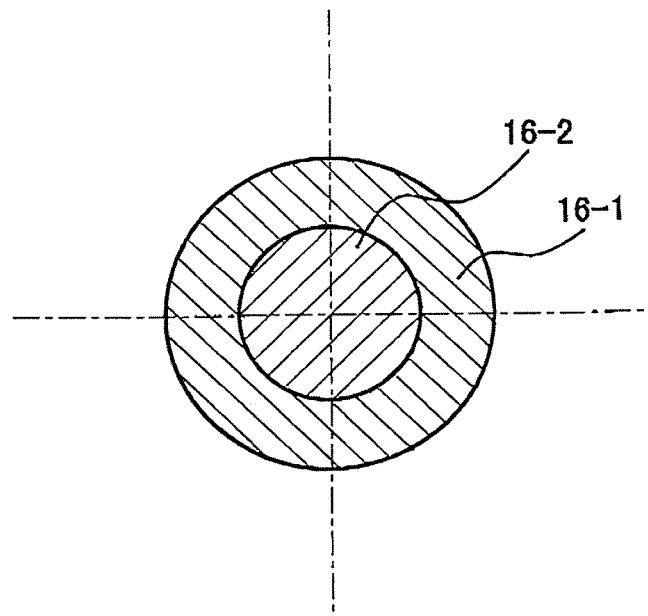
FIG. 6G is a sectional view of the pushing shaft of the two-shaft configuration.
Figure 6H:
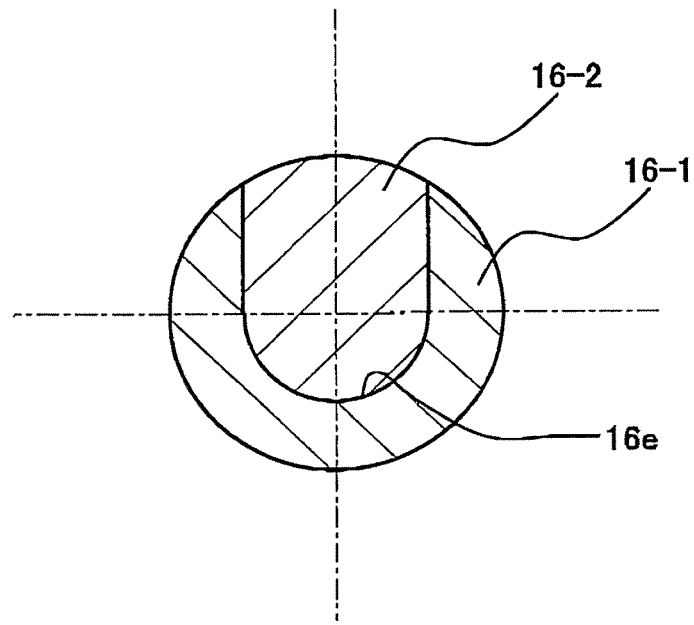
FIG. 6H is a sectional view of a modified example of the pushing shaft having the two-shaft configuration.
Figure 6I:
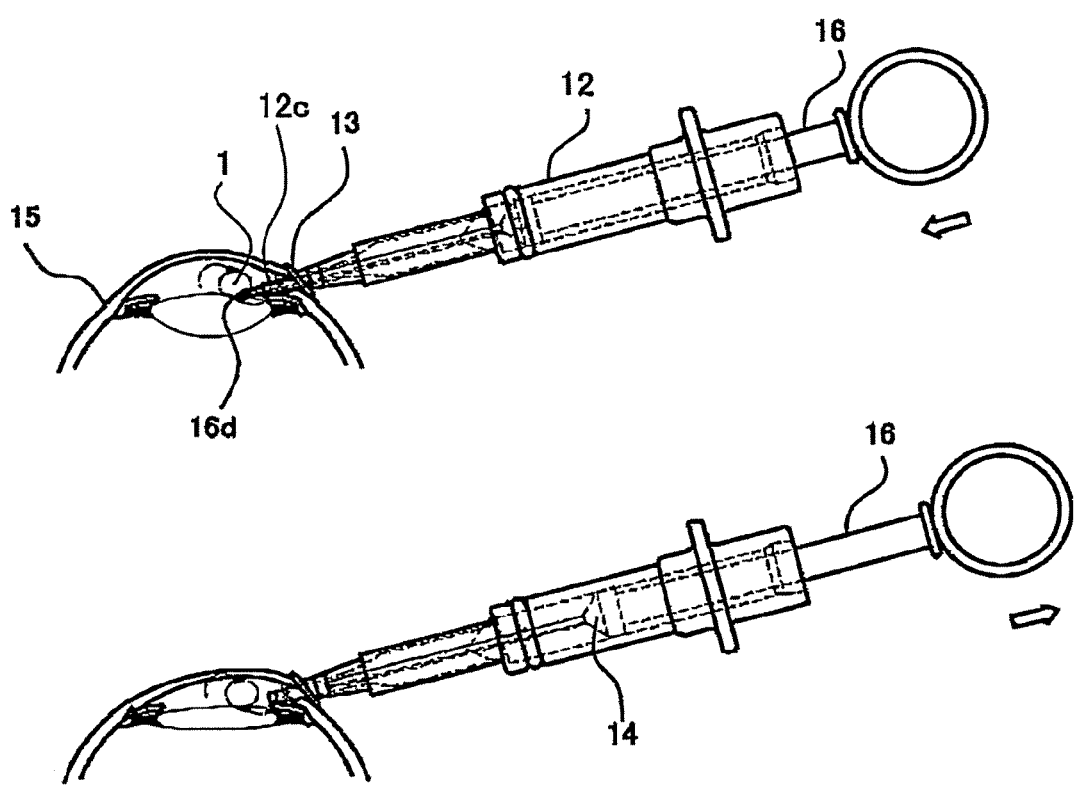
FIG. 6I is a figure for illustrating an operation method of the insertion device shown in FIG. 6E in an operation of the eye.

FIG. 6F and FIG. 6I show an operation using the pushing shaft 16 of the two-shaft configuration and an operation using the pushing shaft 16 of the one-shaft configuration, respectively.

In the operation using the pushing shaft 16 of the one-shaft configuration shown in FIG. 6I, when the pushing shaft 16 is drawn rearward as shown in the lower figure after the nozzle portion 12*c* is inserted into an incision on an eyeball 15 and then the lens 1 is pushed into the eye as shown in the upper figure, the seal cap 14 mounted to the pushing shaft 16 is moved rearward. Thereby, aqueous fluid in the eye is flowed back to the main body 12.

In contrast, in the operation using the pushing shaft 16 of the two-shaft configuration shown in FIG. 6F, even when the pushing member 16-2 is drawn rearward as shown in the lower figure from the state shown in the upper figure, the outer shaft member 16-1 on which the seal cap 14 is mounted is not moved. In other words, only the lens grip portion 16*d* of the pushing member 16-2 is moved rearward. Thereby, the backflow of the aqueous fluid in the eye to the main body 12 is significantly reduced.

When using the insertion devices shown in FIG. 6I and FIG. 6F, the cover ring 13 mounted on the nozzle portion 12*c* is brought into close contact with an area around the incision on the eyeball 15 to limit outflow of the liquid through a gap between the incision and the nozzle portion 12*c*. In such an operation, the use of the pushing shaft 16 of the one-shaft configuration particularly easily causes the above-described backflow of the aqueous fluid. However, the use of the pushing shaft 16 of the two-shaft configuration can effectively reduce the backflow of the aqueous fluid.

Further, as shown in the lower figure of FIG. 6F, after the lens 1 is inserted into the eye, the pushing member 16-2 can be operated to easily perform lens repositioning (e.g., positional adjustment of the support portion 1*b*) in the eye.

Reference character L1 in FIG. 6B denotes the movement amount of the seal cap 14 in the insertion device 2 having the pushing shaft 16 of the two-shaft configuration when the outer shaft member 16-1 is drawn rearward for the introduction of the liquid into the main body 12. The rearward movement of the outer shaft member 16-1 by L1 moves the seal cap 14 rearward by the same amount without changing the position of the lens grip portion 16*d* of the pushing member 16-2.

Reference character L2 in FIG. 6D denotes the movement amount of the lens grip portion 16*d* in the insertion device 2 having the pushing shaft 16 of the two-shaft configuration when the lens repositioning is performed. The rearward movement of the pushing member 16-2 by L2 moves the lens grip portion 16*d* rearward from the inside of the eye into the main body 12 by the same amount without changing the position of the seal cap 14. This enables the lens repositioning with little backflow of the aqueous fluid from the eye into the main body 12.

On the other hand, reference character L3 in FIG. 6E denotes the movement amount of the lens grip portion 16*d* and the seal cap 14 in the insertion device having the pushing shaft 16 of the one-shaft configuration when the lens repositioning is performed. The rearward movement of the pushing shaft 16 by L3 moves not only the lens grip portion 16*d* but also the seal cap 14 rearward by the same amount. This causes the backflow of the aqueous fluid from the eye into the main body 12.

The description was made of the pushing shaft having the concentric two-shaft configuration in which the pushing member (first member) 16-2 is inserted into the through hole 16*k* formed in the outer shaft member (second member) 16-1, which is shown in FIG. 6G. However, other two-shaft configurations may be employed as long as the first and second members can move independently from each other in the axial direction. For example, as shown in FIG. 6H, a U-shaped groove 16*e* extending in the axial direction is formed in a second member 16-1, and a first member 16-2 is put in (held by) the groove 16*e* movably in the axial direction. This two-shaft configuration can prevent the rotation of the first member 16-2 with respect to the second member 16-1 and facilitate forming of the pushing shaft 16 of the two-shaft configuration.

Alternatively, the first and second members may respectively have a lens contact portion that makes contact with and pushes the lens 1.

The assembling procedure (manufacturing method) of the insertion device (intraocular-lens-preloaded type insertion device) 2 configured as described above will be simply described. First, the main body 12 before the pushing shaft 16 is inserted thereinto is prepared. The lens 1 is inserted into the main body 12 from the rear end opening of the main body 12, and then the lens 1 is placed in the lens housing portion 12*b*.

Next, the pushing shaft 16 assembled by inserting the pushing member 16-2 into the through hole 16*k* formed in the outer shaft member 16-1 is inserted into the main body 12 from its rear end opening 12*i*.

Then, the O-ring 32 and cover ring 13 are mounted on the main body 12. Further, the liquid is introduced into the main body 12 by the above-described method, and then the cap 34 is attached to the nozzle portion 12*c* to seal its front end opening 12*j*. Thus, the manufacturing of the intraocular-lenspreloaded type insertion device 2 in which the lens 1 is preliminarily loaded in the lens housing portion 12b is completed.

As described above, the insertion device has the pushing shaft of the two-shaft configuration in which the first and second members can move independently from each other in the axial direction with respect to the main body, so that a sufficient amount of the liquid can be introduced into the main body by moving only the second member, similarly to the syringe. Further, moving the first and second members can insert the lens and liquid into the eye. Moreover, moving only the first member after the insertion of the lens into the eye enables the lens repositioning in the eye while preventing the backflow of the aqueous fluid.

Figure 7:
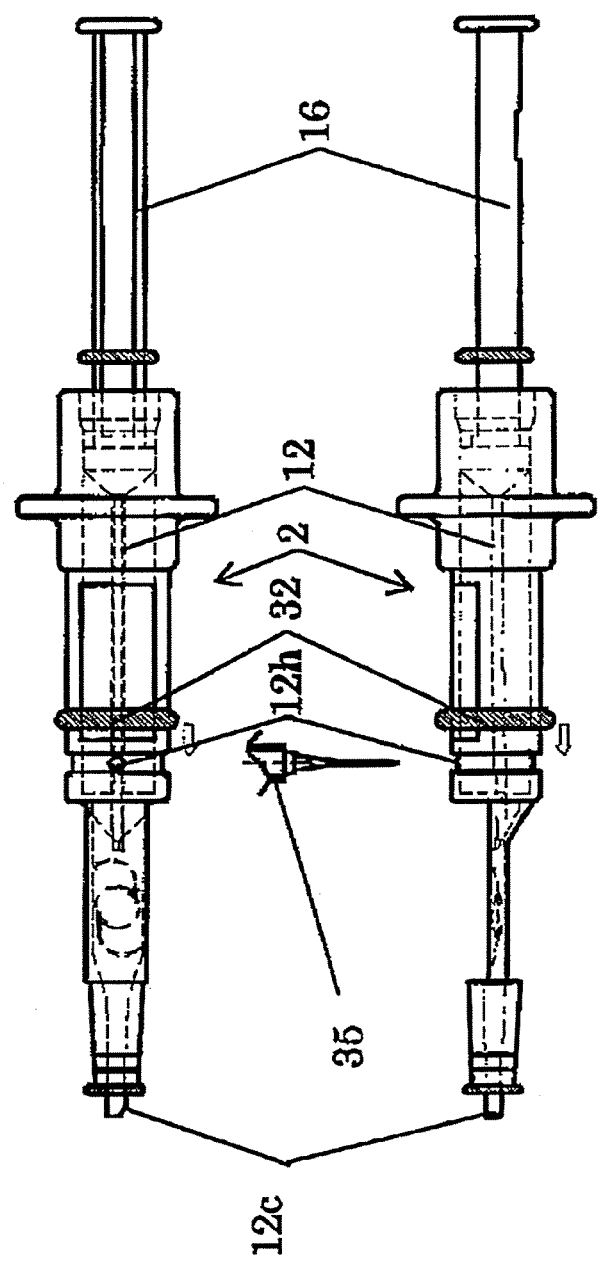
FIG. 7 is a top view and a side view for illustrating a liquid introduction method into the insertion device of the embodiment.

FIG. 7 shows a third liquid introduction method. The O-ring 32 is displaced from the hole 12h formed in the main body 12, the needle of the syringe 35 or a liquid supply device is inserted into the hole 12h to introduce the liquid into the main body 12. Then, the O-ring 32 is moved so as to cover the hole 12h. The outer peripheral surface having the hole 12h is tapered to function as a guide in insertion so as to facilitate insertion of the front end of the needle or the liquid supply device, which further increases operability.

Figure 8:
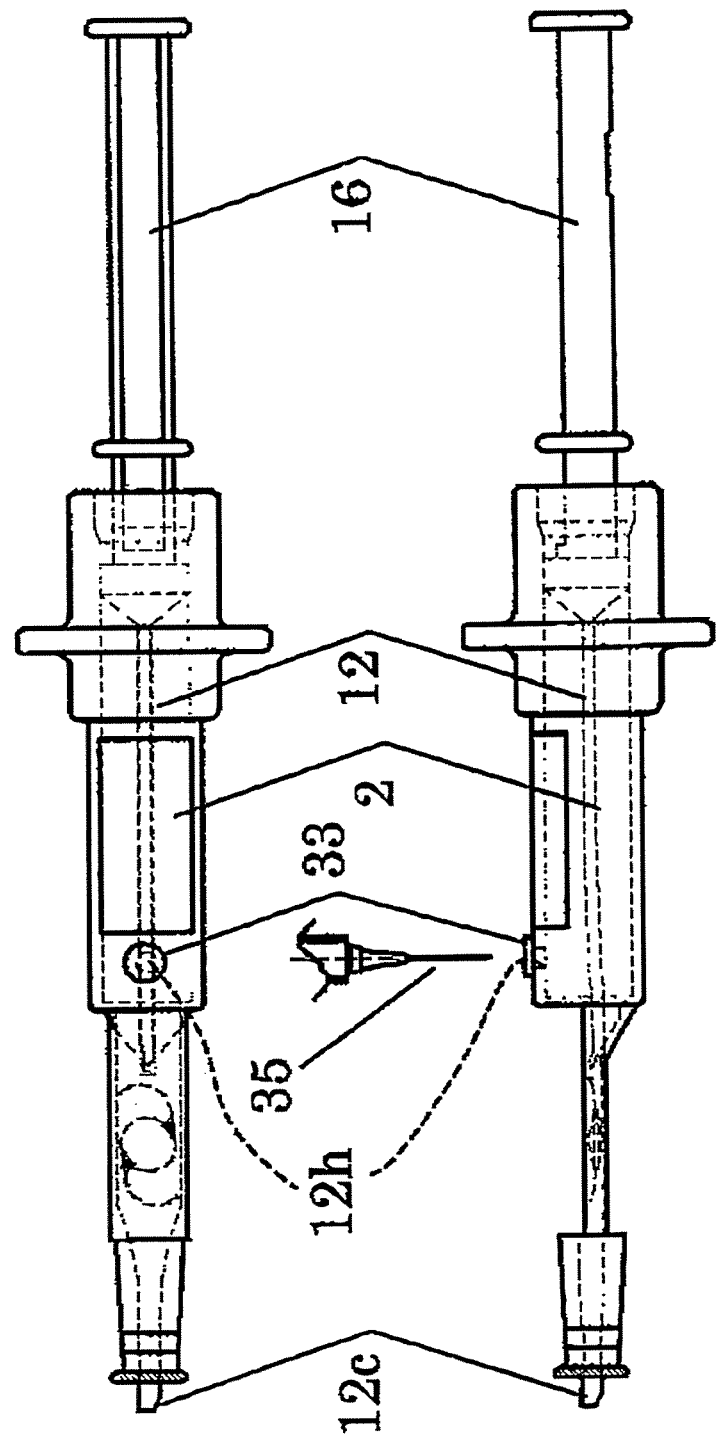
FIG. 8 is a top view and a side view for illustrating a liquid introduction method into the insertion device of the embodiment.

FIG. 8 shows a fourth liquid introduction method. In this method, a plug (a lid) 33 made of an elastic member fitted in the hole 12h is used in place of the O-ring 32. The needle of the syringe 35 is inserted into the plug 33 to introduce the liquid in the syringe into the main body 12. The plug 33 can prevent leakage of the liquid because a hole after removal of the needle is closed by elasticity thereof. In order to prevent the plug 33 from being removed from the hole 12h, it is recommended to devise the shape of the plug 33. For example, a portion of the plug 33 fitted in the hole 12h preferably has an increasing thickness toward the bottom. The plug 33 may be bonded to the main body 12.

Figure 9:
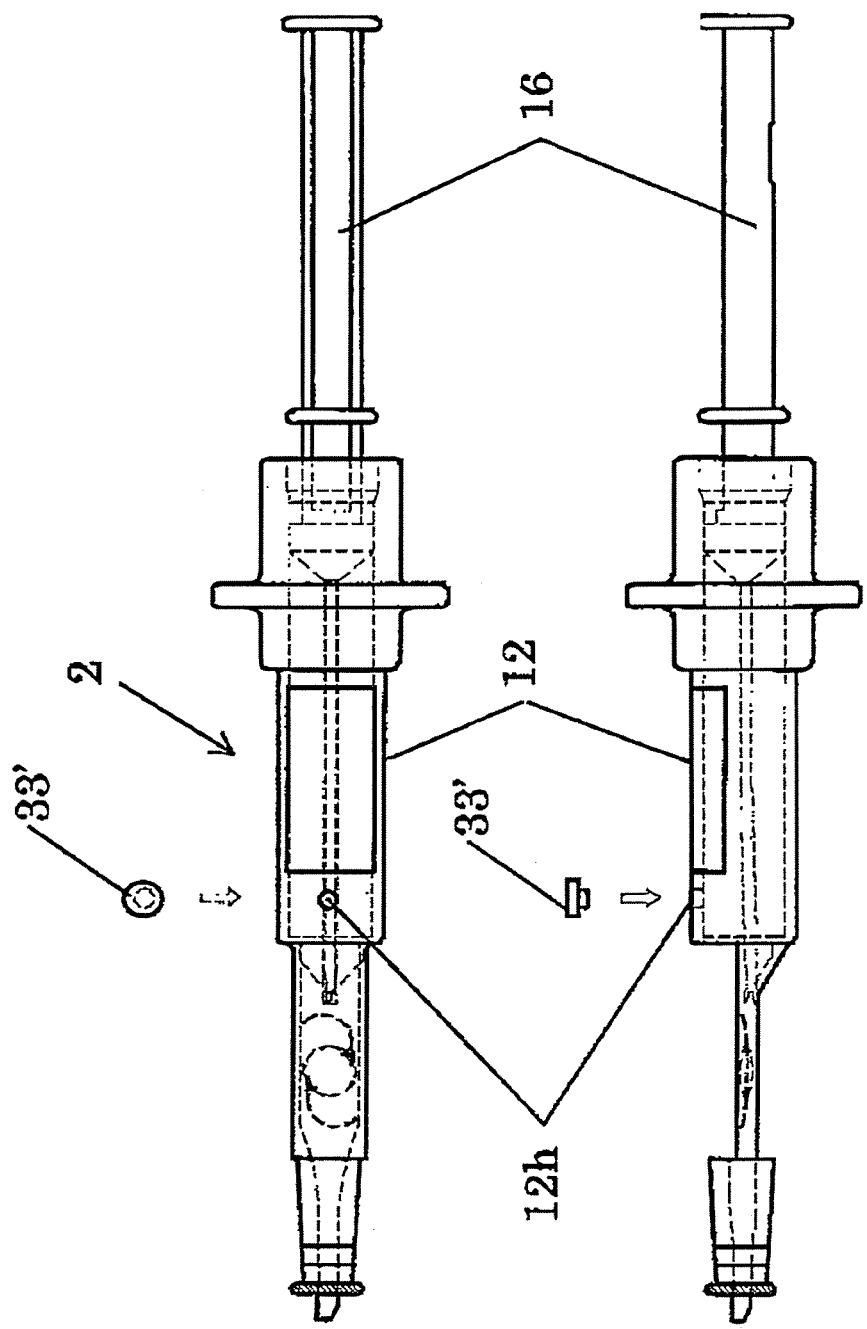
FIG. 9 is a top view and a side view for illustrating a liquid introduction method into the insertion device of the embodiment.

FIG. 9 shows a fifth liquid introduction method. Similarly to the third method, the needle of the syringe 35 or the liquid supply device is inserted into the hole 12h to introduce the liquid into the main body 12. Then, a lid (a plug) 33' is mounted to the main body 12 so as to cover the hole 12h to prevent the liquid from leaking from the hole 12h. In order to prevent the lid 33' from being removed from the hole 12h, it is recommended to devise the shape of the lid 33'. For example, a portion of the lid 33' fitted in the hole 12h preferably has an increasing thickness toward the bottom. The lid 33' may be bonded to the main body 12.

If use of the insertion device without the plug 33 or the O-ring 32 does not directly influence the flow of the liquid, the use of the plug 33 or the O-ring 32 is not necessarily required.

Figure 10:
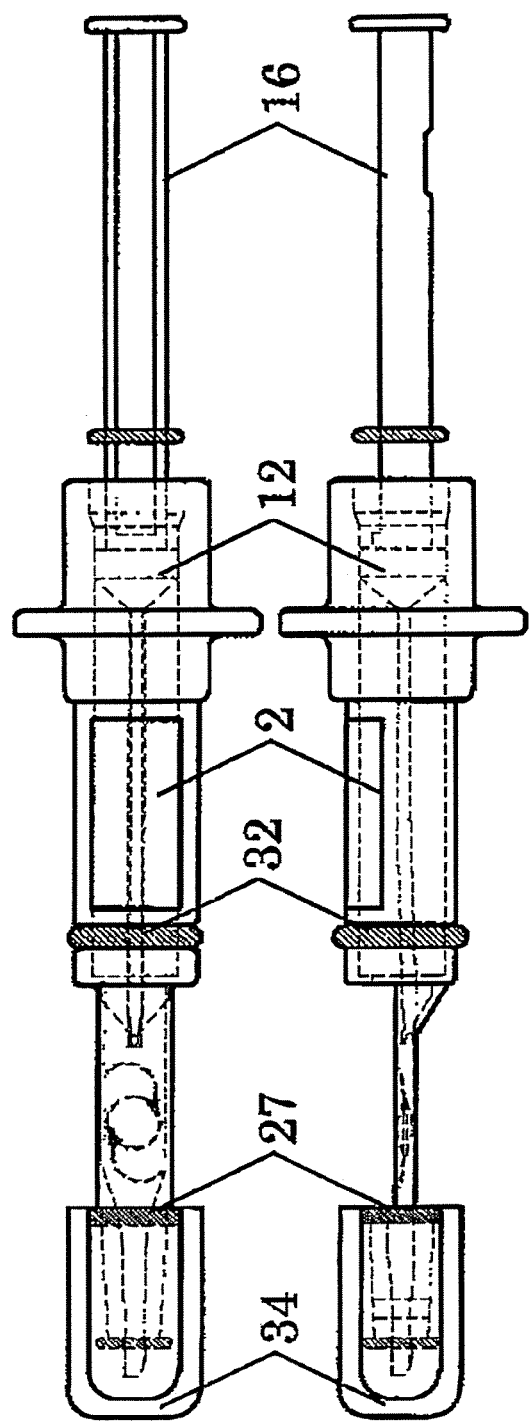
FIG. 10 is a top view and a side view for illustrating a storage method of the insertion device of the embodiment.

According to the liquid introduction method described above, the liquid can be easily introduced into the main body 12 immediately before an operation or before factory shipment of the insertion device. When the liquid is introduced before factory shipment and then shipped, transported, and stored, the nozzle portion 12c is preferably covered with the cap 34 in FIG. 10 in order to prevent leakage of the liquid outside during the shipment, transportation and storage.

The cap 34 has no opening in the front end and the peripheral wall portion, and has an opening in the rear end. A seal ring 27 made of an elastic member is mounted to the inside of the rear end. The cap 34 is mounted so that the seal ring 27 is brought into tight contact with the outer peripheral surface of the nozzle portion 12c (or the lens housing portion 12b) to form a closed space around the nozzle portion 12c. Thus, even if the liquid leaks from the front end opening 12j into the cap 34, the liquid does not leak outside. This also prevents vaporization of the liquid and damage to the nozzle portion 12c. Thus, the lens 1 as well as the liquid can be held in the insertion device 2 and stored for a long time.

In the case of an operation, the cap 34 is removed if mounted, and the front end (a portion to be inserted into an eye) of the nozzle portion 12c is inserted into the eye through an incision formed in an eyeball. Then, the pushing shaft 16 is pushed into the main body 12. Thus, the liquid in the main body 12 starts to be introduced into the eye through the front end opening 12j of the nozzle portion 12c, and the lens 1 with the optical portion 1a held by the lens grip portion 16d starts to be moved from on the lens holding member 28 in the front end direction. The lens 1 is folded and deformed into a small shape with movement in the nozzle portion 12c, and pushed into the eye through the front end opening 12j.

Figure 11:
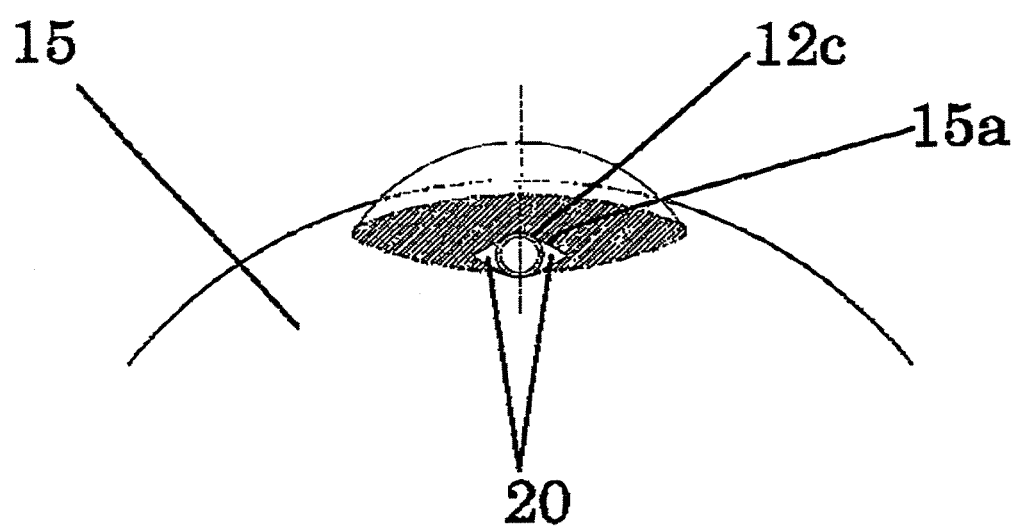
FIG. 11 shows an incision formed in an eyeball.

It can be expected that the liquid is introduced into the eye from the nozzle portion 12c to increase ocular tension and inflate the anterior chamber, thereby forming an insertion space for the lens 1. As shown in FIG. 11, however, in a state in which the nozzle portion 12c is inserted into an incision 15a in an eyeball 15, the incision 15a has a larger area than the nozzle portion 12c, thereby creating a gap (a region outside the nozzle portion 12c) 20 between the periphery of the incision 15a and the outer peripheral surface of the nozzle portion 12c. Thus, the liquid once introduced into the eye leaks from the gap 20, and in particular, when the amount of liquid introduced into the main body 12 is relatively small (for example, about 0.5 to 2.5 ml), the ocular tension cannot be increased and the anterior chamber cannot be sufficiently inflated.

Thus, in the embodiment, the cover ring 13 provided near the front end of the nozzle portion 12c is pressed against the eyeball 15 to cover the gap 20 in the incision 15a. In this case, the cover ring 13 may completely or partly cover the gap 20. This can restrict (prevent or reduce the amount of) the flow of the liquid from the gap 20, and even if the amount of the liquid introduced into the main body 12 is relatively small, the ocular tension can be reliably increased to sufficiently inflate the anterior chamber. When the ocular tension becomes too high, the insertion device 2 is displaced rearward so as to separate the cover ring 13 from the eyeball 15, and the liquid flows out of the gap 20 of original size, thereby reducing the ocular tension.

In this manner, according to the embodiment, the lens 1 can be inserted into the eye and also the ocular tension can be controlled simply by an operation on hand of the operator.

In the embodiment, the case has been described where the cover ring 13 as a separate member from the nozzle portion 12c is used for covering the gap 20 in the incision 15a in the eyeball 15, but a ring-shaped portion having the same function as the cover ring 13 may be formed integrally with the nozzle portion 12c.

Now, the results of experiments on the functions of the cover ring 13 and a cover-ring-shaped portion having the same function and the results of experiments on optimization of the front end shape of the nozzle portion 12c will be shown.

Figure 12:
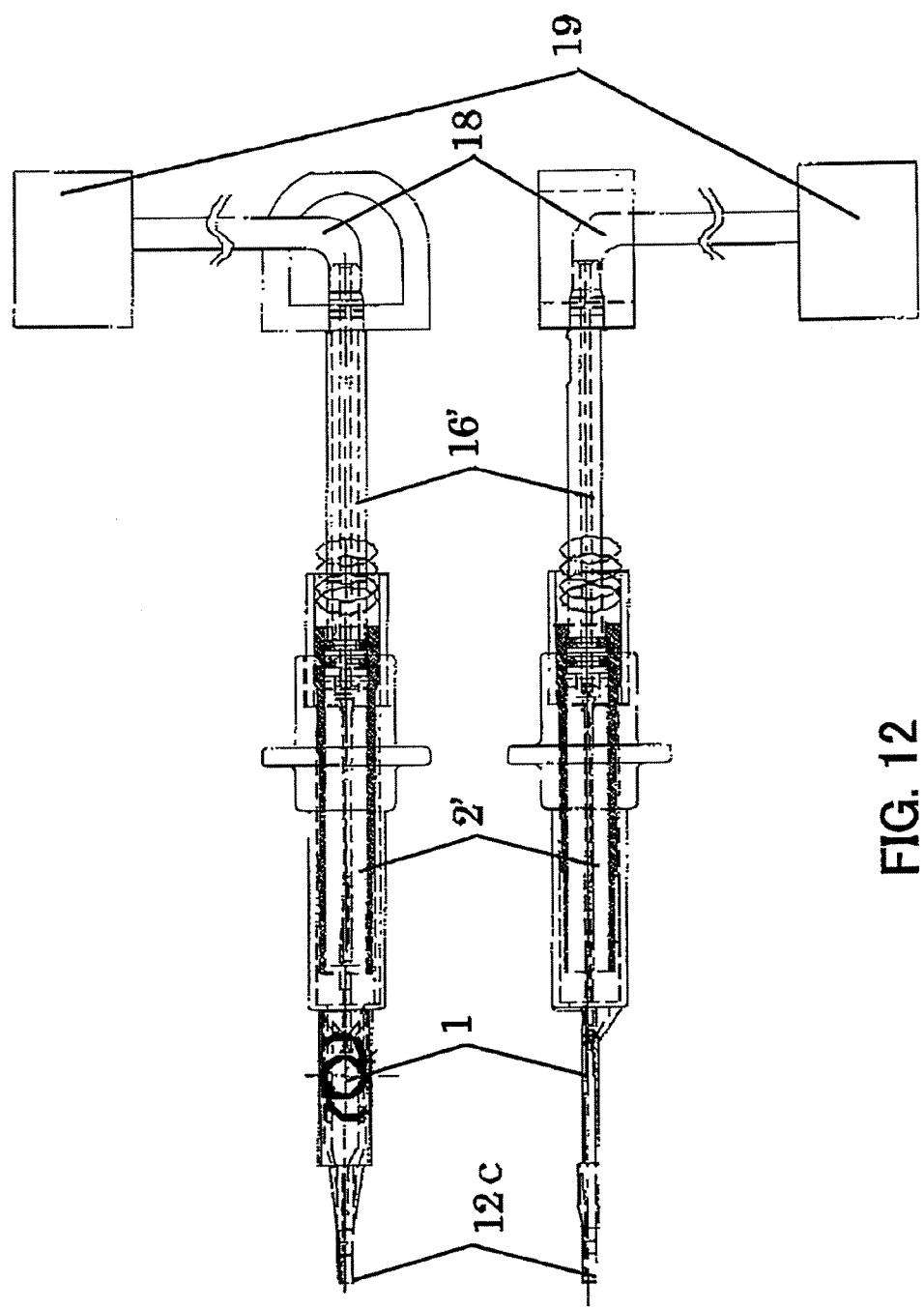
FIG. 12 is a top view and a side view of an insertion device of a comparative example for the embodiment.

Experiment 1: First, as shown in FIG. 12 (the upperside shows a top view and the lowerside shows a side view), a device 19 for supplying a liquid such as physiologic saline was connected to an insertion device 2' via a tube 18 and an experiment was conducted. At this time, the insertion device 2' did not have a cover ring 13 or a configuration corresponding thereto. A flow path through which the liquid passes was provided in a pushing shaft 16', and the tube 18 was connected to the pushing shaft 16'.

When the liquid was continuously introduced into the eyeball from the liquid supply device 19 via the insertion device 2' (a nozzle portion 12c), it was confirmed that ocular tension increased and the anterior chamber was filled with the liquid, and the posterior capsule of the crystalline lens moved toward the vitreous body (the anterior chamber was inflated). It was found that when the liquid of a predetermined flow rate can be continuously supplied from the liquid supply device 19 to the eyeball, the cover ring 13 or the configuration corresponding thereto needs not to be provided in the nozzle portion 12c.

Figure 13:
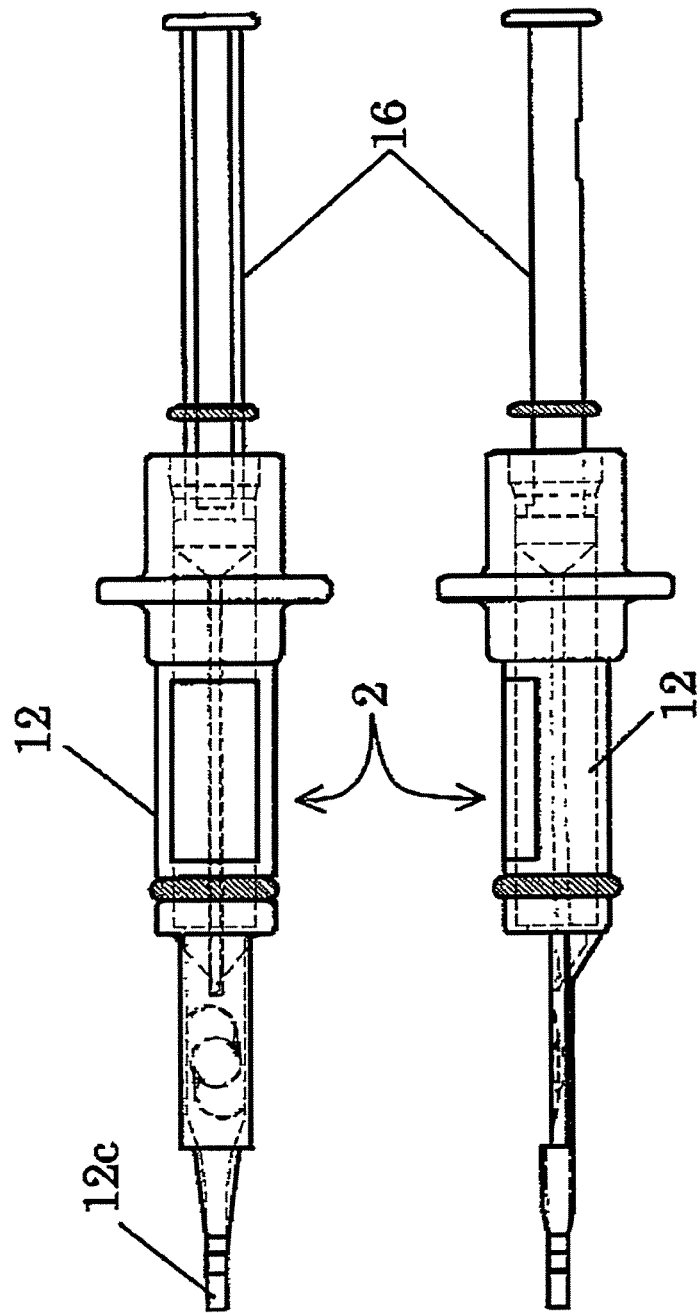
FIG. 13 is a top view and a side view showing a state in which a cover ring is removed from the insertion device of the embodiment.
Figure 14:
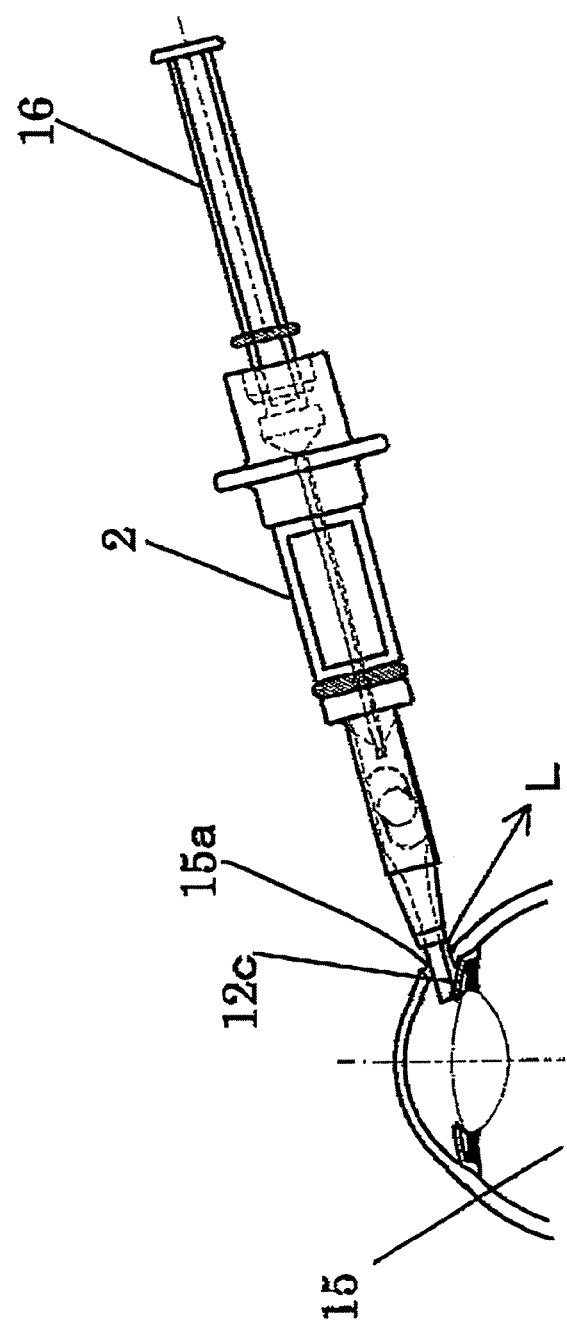
FIG. 14 is a sectional view showing a state of an eyeball when a lens is inserted using the insertion device in FIG. 13.

Experiment 2: An experiment was conducted using an insertion device 2 in which a liquid of 25 ml was previously introduced into a main body 12 as shown in FIG. 13. In this experiment, a nozzle portion 12c did not have a cover ring 13 or a configuration corresponding thereto. In this case, even if a pushing shaft 16 was pushed to introduce most of the liquid in the main body 12 into the eye, ocular tension hardly increased from ocular tension when an incision was formed, and the posterior capsule of the crystalline lens did not move toward the vitreous body. The reason that the ocular tension did not increase was studied and found. It was because the incision was linearly formed by a knife, and the three-dimensional nozzle portion 12c was inserted into the incision to form a gap 20 in FIG. 11, and a liquid L leaked from the gap 20 as shown in FIG. 14.

Figure 15:
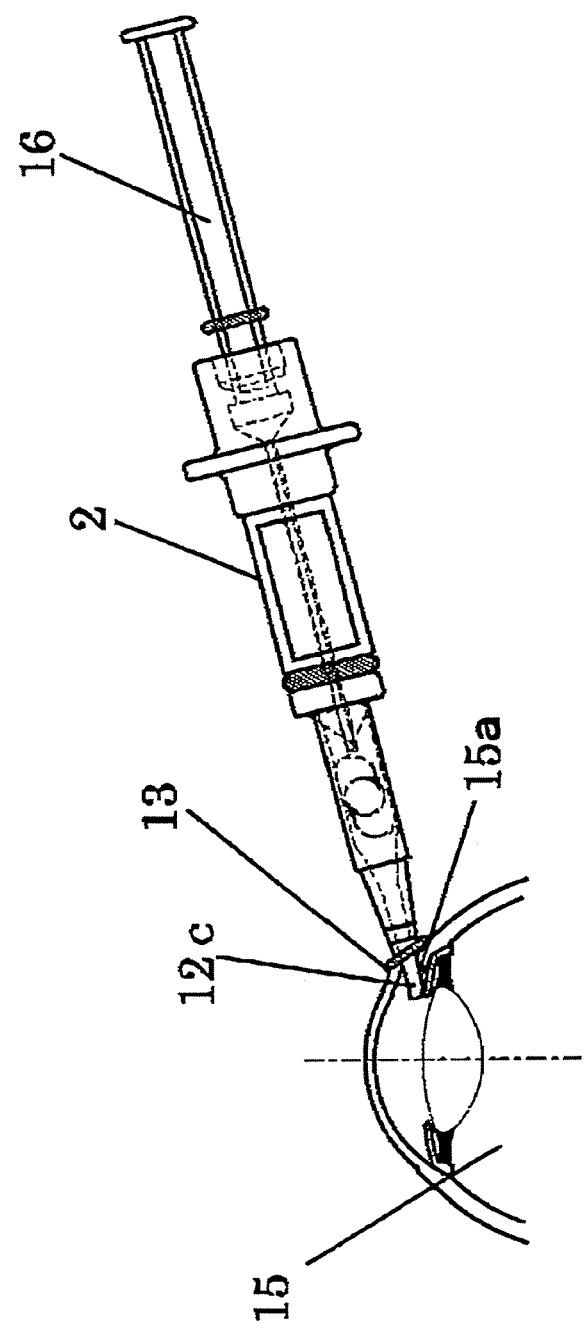
FIG. 15 is a sectional view showing a state of an eyeball when a lens is inserted using the insertion device of the embodiment.

Experiment 3: A cover ring 13 was mounted to the nozzle portion 12c of the insertion device 2 used in Experiment 2, and the cover ring 13 was brought into tight contact with a portion near the incision 15a in the eyeball 15 as shown in FIG. 15, and an experiment similar to Experiment 2 was conducted. In this case, ocular tension increased and the posterior capsule of the crystalline lens moved toward the vitreous body. It was confirmed that this was because a gap 20 is created outside the nozzle portion 12c in the incision 15a, but the cover ring 13 is brought into tight contact with around the incision 15a in the eyeball 15, and thus even if the liquid flows out of the gap 20, a seal by the cover ring 13 prevents the liquid from leaking outside. In particular, the cover ring 13 has a circular section, and thus the cover ring 13 is brought into ring-shaped line contact around the incision 15a in the eyeball 15. Thus, it can be considered that a sealing effect was able to be obtained more easily and reliably than the case of a seal by surface contact.

As described above, a step 12c1 was provided in the nozzle portion 12c to prevent the cover ring 13 from moving rearward on the nozzle portion 12c. Also, a tilt of the cover ring 13 on the nozzle portion 12c was allowed to stably maintain a tight contact state of the cover ring 13 on the eyeball 15.

Figure 16A:
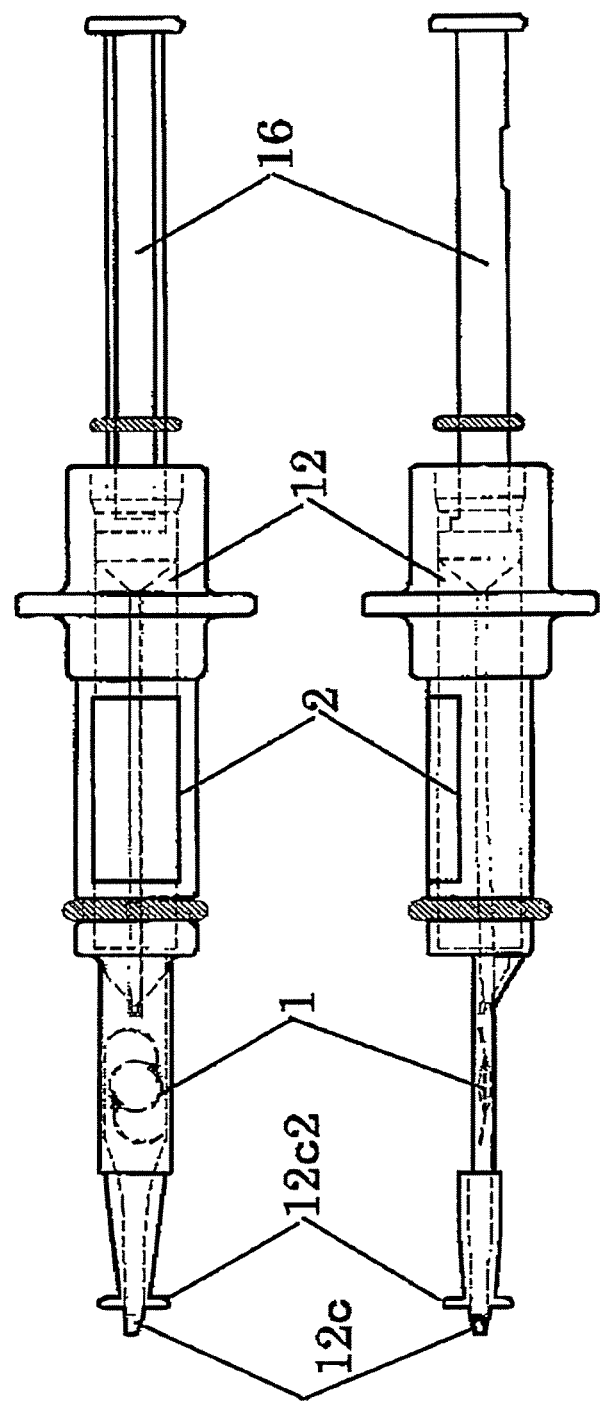
FIG. 16A is a top view and a side view of an insertion device of a comparative example for the embodiment.

Experiment 4: As shown in FIG. 16A, a ring-shaped portion 12c2 having substantially the same shape as the cover ring 13 was formed integrally with the nozzle portion 12c, and an experiment similar to Experiments 2 and 3 was conducted. In this case, the ring-shaped portion 12c2 had little flexibility. Thus, the ring-shaped portion 12c2 was able to be partly brought into tight contact with the eyeball 15, but other portions was not able to be brought into tight contact with the eyeball 15, and the liquid leaked outside from a gap between the eyeball 15 and the ring-shaped portion 12c2. Thus, ocular tension hardly increased.

Figure 16B:
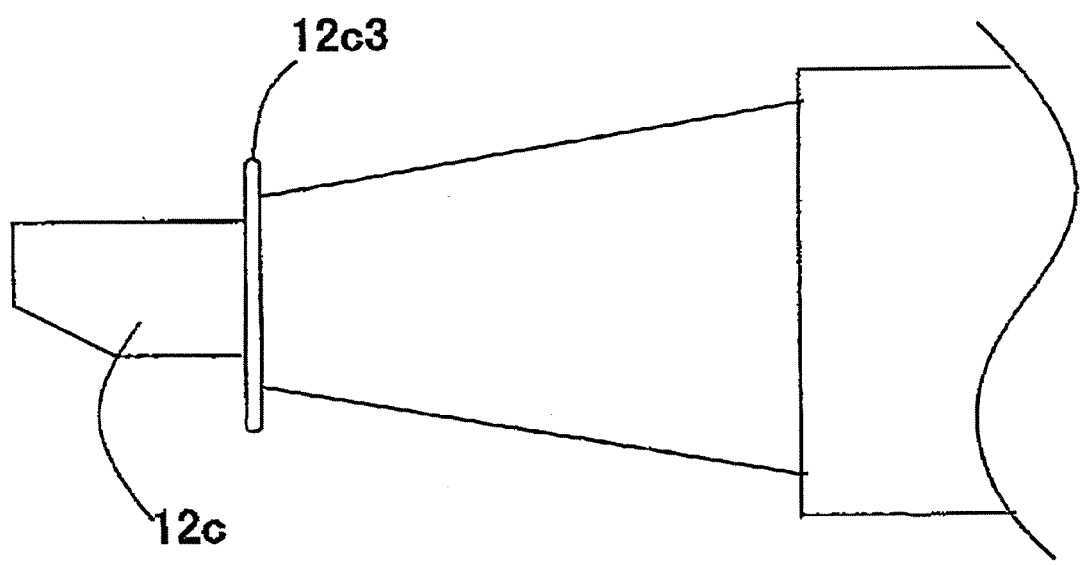
FIG. 16B is a side view of a nozzle portion of an insertion device of an embodiment (a modified example)

As shown in FIG. 16B, however, it was found that a ring-shaped portion (a cover-ring-shaped portion) 12c3 is formed to have a thickness of about 0.3 mm and have flexibility, and thus the entire circumference of the cover ring-shaped portion 12c3 can be brought into tight contact with the eyeball 15, and a sealing effect equal to the seal ring 13 can be obtained.

Figure 17A:
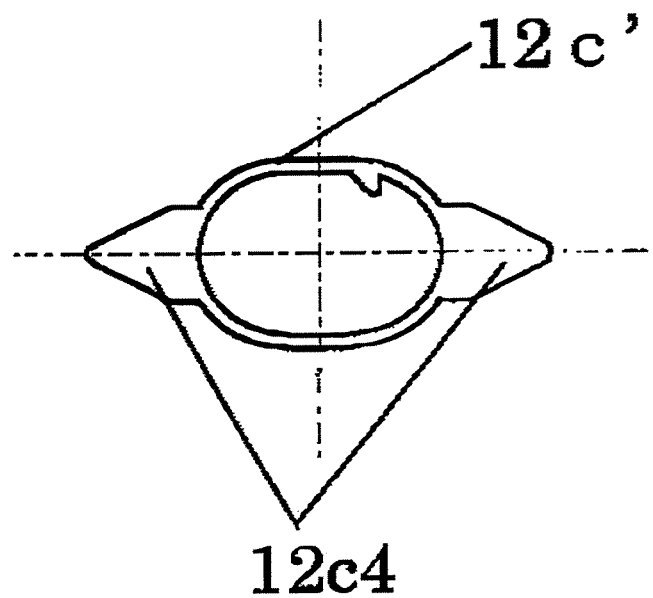
FIG. 17A is a sectional view of a nozzle portion of an insertion device of an embodiment (a modified example)
Figure 17B:
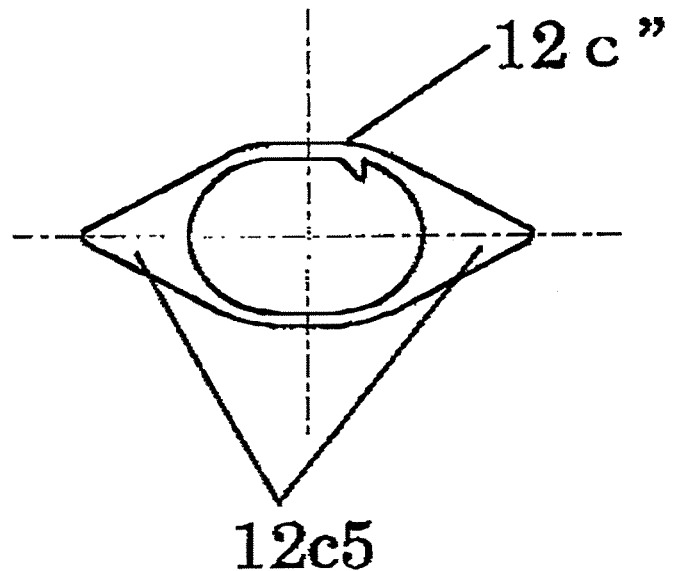
FIG. 17B is a sectional view of a nozzle portion of an insertion device of an embodiment (a modified example)

Experiment 5: FIGS. 17A and 17B show the shape of a section of a nozzle portion 12c of an insertion device used in this experiment. As shown in FIG. 11, when the nozzle portion 12c having a circular section or an oval section is inserted into the incision 15a, the incision 15a is opened to a substantially rhombic shape. Then, gaps 20 each having a substantially triangular shape are formed between the nozzle portion 12c and the edges of the incision 15a.

Thus, in this experiment, nozzle portions 12c' and 12c'' having protruding incision covering shapes 12c4 and 12c5 that can substantially fill the gaps 20 were formed, and an experiment similar to Experiments 2 to 4 was conducted. In this case, the gaps created between the nozzle portions 12c' and 12c'' and the edges of the incision 15a were reduced in size or eliminated, and thus the leakage of the liquid from the eyeball 15 was reduced or prevented to increase the ocular tension.

In this manner, it was found that the nozzle portion itself is formed to have the shape that can fill the gaps 20 to obtain a sealing effect equal to the case where the cover ring 13 or the cover-ring-shaped portion 12c3 is provided in the nozzle portion 12c.

It is considered that a higher sealing effect can be obtained by providing the cover ring 13 or the cover-ring-shaped portion 12c3 in the nozzle portion having the protruding incision covering shapes 12c4 and 12c5.

Experiment 6: As in Experiments 3 and 4, providing the cover ring 13 or the cover-ring-shaped portion 12c3 in the nozzle portion 12c can increase ocular tension. It is more preferable to provide the configuration for adjusting ocular tension to proper one when the ocular tension becomes too high to the contrary.

Figure 18:
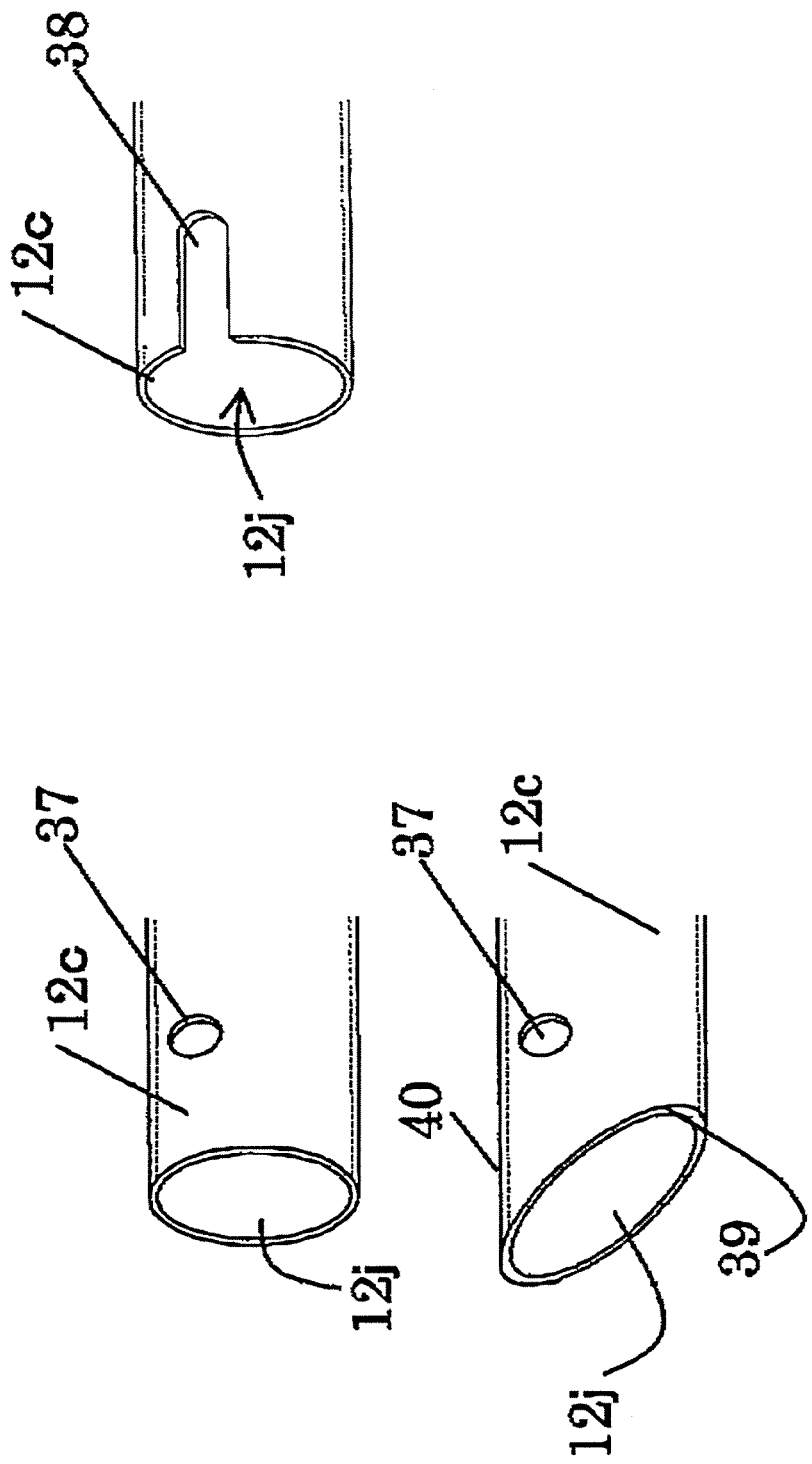
FIG. 18 is a perspective view of a nozzle portion of an insertion device of an embodiment (a modified example)

In this experiment, as shown in FIG. 18, an opening such as a hole 37 or a slit 38 was provided on the front end side of the nozzle portion 12c from the cover ring 13 or the cover-ring-shaped portion 12c3. Also, an inclined portion 39 was formed in the front end of the nozzle portion 12c.

When the ocular tension becomes too high, the insertion device 2 is slightly drawn from the eyeball so that part of the hole 37, the slit 38 or the inclined portion 39 is exposed to the outside of the eye, and thus a liquid flowing from the main body 12 to the front end opening 12j of the nozzle portion 12c or a liquid in the eye is ejected to the outside of the eye through the hole 37 or the like. This facilitates adjustment of the ocular tension.

For increasing the ocular tension again because it becomes too low, the hole 37 or the like may be placed in the eye to bring the cover ring 13 or the cover-ring-shaped portion 12c3 into tight contact with the eyeball.

Experiment 7: When the nozzle portion 12c is inserted into a linear incision, ocular tension is still low and the incision is not opened. Thus, it is difficult to insert the nozzle portion 12c even if the front end thereof has an inclined shape to some extent. On the other hand, merely forming the front end of the nozzle portion 12c to have an excessively inclined shape for facilitating insertion of the nozzle portion 12c into the linear incision increases movement resistance (friction resistance) of the lens 1 in the nozzle portion 12c, and places an excessive load on the lens 1.

Figure 19:
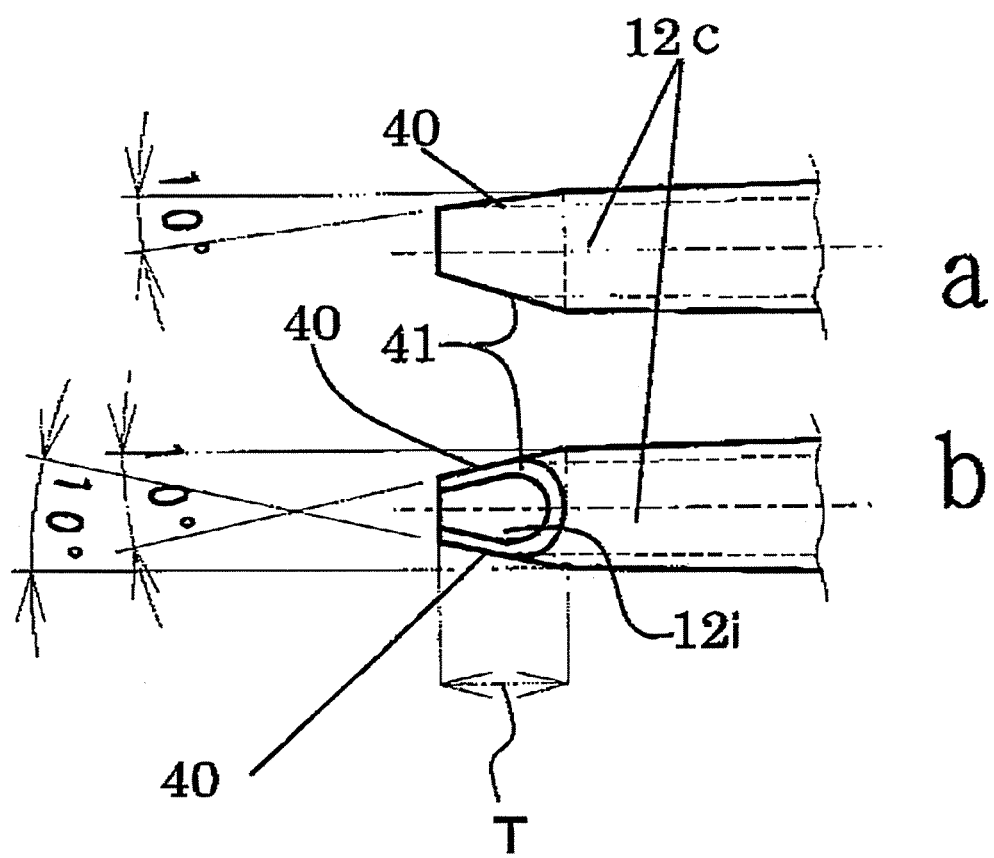
FIG. 19 is a side view and a bottom view of a nozzle portion of an insertion device of an embodiment (a modified example)

Thus, an experiment was conducted by changing the front end shape of the nozzle portion 12c in various manners. One of the shape is as shown in FIG. 19 (the upperside is a side view and the lowerside is a bottom view). In FIG. 19, an inclined portion 41 was first provided on the lower side of the front end of the nozzle portion 12c. A peripheral wall from the front end of the inclined portion 41 (the front end of the nozzle portion 12c) to the rear end of the inclined portion 41 is hereinafter referred to as a front end peripheral wall T.

The front end peripheral wall T was formed over the entire circumference to be a tapered surface 40 inclined by an angle of 10° or more in a tapering direction with respect to a peripheral wall closer to the front end than the peripheral wall T.

This facilitated insertion of the nozzle portion 12c into an incision in an eyeball with low ocular tension.

On the other hand, when the inclination angle of the front end peripheral wall was 9° or less with respect to the peripheral wall closer to the rear than the front end peripheral wall, insertion of the nozzle portion 12c into the incision was difficult.

When the tapered surface 40 having an angle of 10° or more is formed from a position closer to the rear than the rear end of the inclined portion 41, the taper excessively reduces a space in the nozzle portion to excessively increase friction resistance when the lens 1 passes through the space in the nozzle portion.

In this respect, as in this experiment, the tapered surface 40 is formed on the front end side from the rear end of the inclined portion 41 to prevent an increase in friction resistance when the lens 1 passes through the inside of the nozzle portion 12c. Further, when the lens 1 passes the rear end of the inclined portion 41, deformation of the lens 1 is released and a stress generated in the lens 1 by the deformation is released, thereby reducing friction resistance. This facilitated insertion of the nozzle portion 12c into the incision in the eyeball with low ocular tension, and achieved the nozzle portion 12c with a light load on the lens 1.

Figure 22:
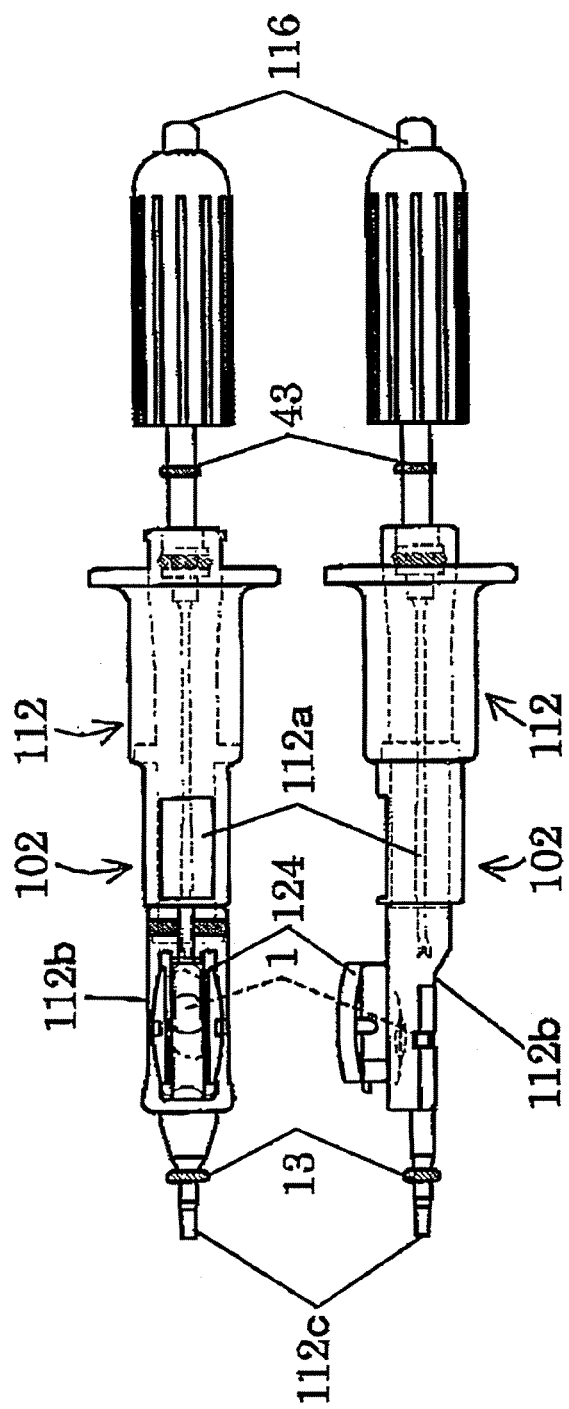
FIG. 22 is a top view and a side view of an insertion device (of a conventional type) of an embodiment.

Experiment 8: The configuration in which the cover ring 13 or the cover-ring-shaped portion 12c3 described in Experiments 3 and 4, or the protruding incision covering shapes 12c4 and 12c5 is provided in the nozzle portion may be applied not only to the insertion device of the embodiment but to the conventional type insertion device as shown in FIG. 20. FIG. 22 shows an insertion device in FIG. 20 provided with a cover ring 13 in a nozzle portion. In this experiment, a viscoelastic material was used as a lubricant.

The cover ring 13 was provided in the nozzle portion 112c of the insertion device 102 to bring the cover ring 13 into tight contact with the eyeball 15 similarly to Experiments 3 and 4. Thus, the amount of flow of the viscoelastic material in the eye from the incision was able to be reduced.

The O-ring 43 described above is mounted on the pushing shaft 116 of the insertion device 102 in FIG. 22. In this manner, the O-ring 43 may be used in the conventional type insertion device 102 in FIG. 20.

Figure 23A:
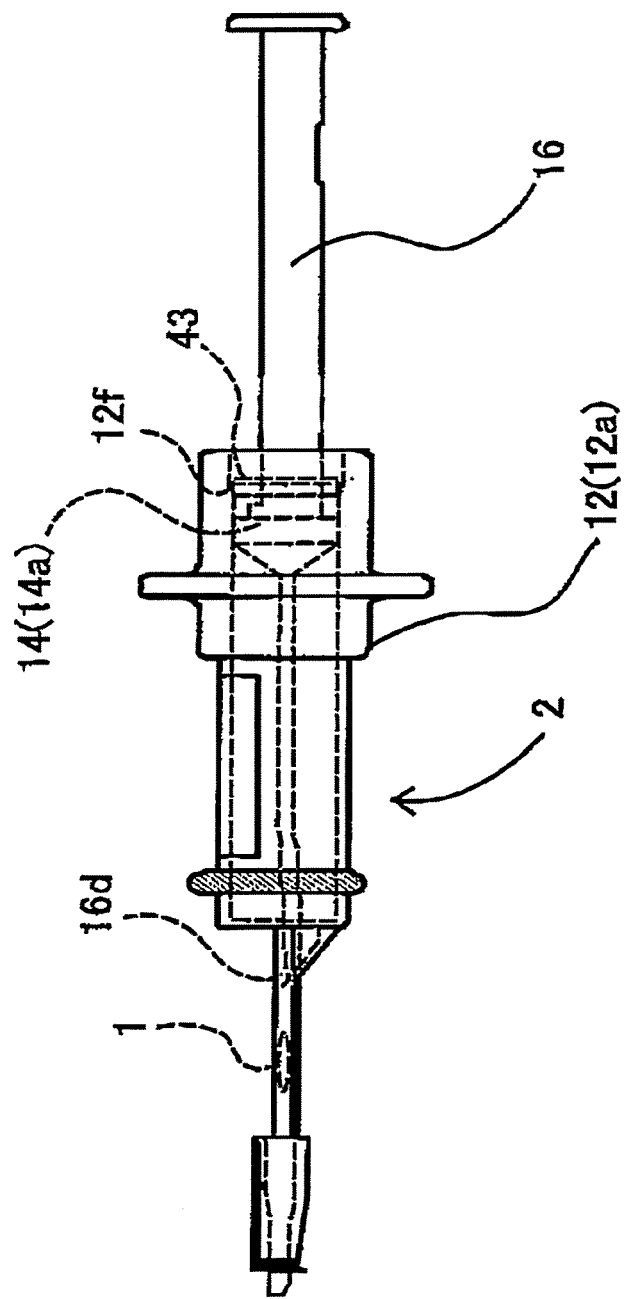
FIG. 23A is a side view showing an assembly completion state of the insertion device of the embodiment.

Next, the function of the O-ring 43 will be described with reference to FIGS. 23A and 23B. As shown in FIG. 23A, in an assembly completion state of the insertion device 2 (before pushing of the pushing shaft 16), the O-ring (the second elastic member) 43 that contacts the conical surface 12f formed in the inner periphery of the rear end of the outer cylindrical portion 12a and the seal cap 14 (the ring portion 14a: the first elastic member) secured to the pushing shaft 16 are close to each other. However, even in this state, the pushing shaft 16 is supported by two points: the ring portion 14a of the seal cap 14 and the O-ring 43 with respect to the main body 12, and thus as compared with the case where the pushing shaft 16 is supported only by the ring portion 14a of the seal cap 14, vertical and lateral displacement of the pushing shaft 16 relative to the main body 12 can be suppressed.

Figure 23B:
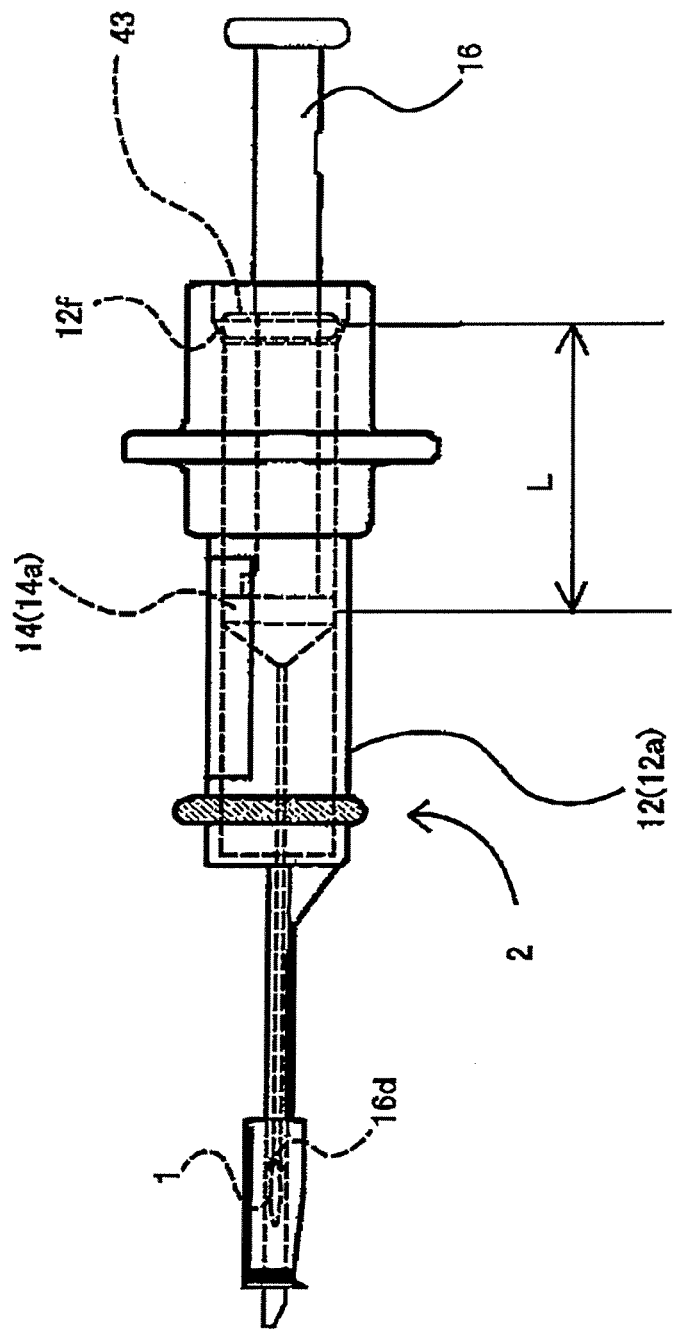
FIG. 23B is a side view showing a lens pushing state of the insertion device of the embodiment.

When the pushing shaft 16 is pushed in the front end direction in this state as shown in FIG. 23B, the seal cap 14 secured to the pushing shaft 16 is moved with the pushing shaft 16 in the front end direction, while the O-ring 43 mounted axially movably relative to the pushing shaft 16 is prevented from moving in the front end direction by the conical surface 12f, and thus remains in a position where the O-ring 43 contacts the conical surface 12f. This increases a distance L between the ring portion 14a of the seal cap 14 and the O-ring 43. Thus, as compared with the state before pushing of the pushing shaft 16, vertical and lateral displacement of the pushing shaft 16 relative to the main body 12 can be minimized. Thus, the front end (the lens grip portion 16d) of the pushing shaft 16 can be precisely guided with respect to the optical portion 1a of the lens 1 held by the lens holding member 28, and the lens 1 can be properly pushed out.

The O-ring 43 may be mounted on the pushing shaft 16 or may be secured to the inner periphery of the main body 12. A plurality of members corresponding to the O-ring 43 may be provided rather than one. Further, a plurality of O-rings 43 are placed axially adjacent to each other, and brought into press contact with the inner peripheral surface of the main body 12 and the outer peripheral surface of the pushing shaft 16 to provide the sealing function, thus leakage of the liquid from the rear end opening 12i of the main body 12 can be more reliably prevented in combination with the sealing function of the seal cap 14.

An elastic member corresponding to the O-ring 43 may be secured on the front end side of the main body from the seal cap on the pushing shaft so that the distance between the plurality of elastic members corresponding to the O-ring and the seal cap is reduced from a maximum state to a moderate state with the movement of the pushing shaft in the front and direction. Also in this case, as compared with the case where the elastic member corresponding to the seal cap only is provided, vertical and lateral displacement of the pushing shaft relative to the main body can be minimized, and the lens can be properly pushed out.

As described above, according to the embodiment, the peripheral wall from the lens housing portion to the insertion cylindrical portion is formed without an opening or a gap, thereby reliably preventing the liquid inside from leaking outside. Further, the lens holding member can be inserted into the lens housing portion from the rear, and thus the lens can be easily placed into the lens housing portion.

Further, the lens holding member placed in the lens housing portion can reliably hold the lens in a predetermined shape, and thus the lens is not moved or deformed by the flow of the liquid in the main body, and the insertion device housing the lens can be properly stored. In this case, the need for introducing the liquid into the insertion device immediately before an operation is eliminated, thereby reducing a burden on an operator or an assistant.

The cover portion that covers at least part of the incision in the eye is provided in the insertion cylinder, and thus the amount of leakage, from the gap in the incision, of the liquid that is supplied into the eye from the insertion cylinder can be restricted. Thus, even if the amount of liquid supplied into the eye is small, ocular tension can be increased to sufficiently inflate the anterior chamber, thereby allowing the lens to be smoothly inserted into the eyeball.

Further, the plurality of elastic members are placed between the pushing shaft and the main body so that the distance therebetween is changeable with movement of the pushing shaft relative to the main body, and thus for example, the distance between the plurality of elastic members is increased with movement of the pushing shaft in a lens insertion direction. The plurality of elastic members are provided to minimize radial displacement of the pushing shaft relative to the main body. Thus, the front end of the pushing shaft can be precisely guided with respect to the lens, and the lens can be properly pushed out.

In the embodiment, a so-called preload type insertion device (intraocular-lens-preloaded type insertion device) has been described in which the lens 1 is previously set in the lens housing portion 12b before factory shipment (before delivery to a hospital). However, alternative embodiments of the present invention may include other types of insertion devices. For example, an insertion device in which it is stored separately from a lens and the lens 1 is set immediately before an operation can be used.

Furthermore, the present invention is not limited to these preferred embodiments and various variations and modifications may be made without departing from the scope of the present invention.

This application claims foreign priority benefits based on Japanese Patent Applications Nos. 2006-139560, filed on May 18, 2006, 2006-139561, filed on May 18, 2006 and 2006-155051, filed on Jun. 2, 2006 and each of which is hereby incorporated by reference herein in its entirety as if fully set forth herein.

What is claimed is:

1. An insertion device for an intraocular lens comprising:
a main body in which the lens is placed; and
a pushing shaft having a two-shaft configuration with a pushing member and an outer shaft member that are concentrically assembled and movable independently from each other in an axial direction of the device with respect to the main body, said outer shaft member being movable along an inner peripheral surface of said main body with keeping in contact with said inner peripheral surface, said pushing member pushing out the lens from the main body into an eye through a nozzle portion,
wherein the pushing member and the outer shaft member are configured so that a liquid is introduced into the main body through the nozzle portion when the outer shaft member is drawn rearward while fixing the pushing member without movement to locate a lens grip portion of the pushing member slightly reward of the lens.

2. The insertion device according to claim 1, wherein the pushing member makes contact with and pushes the lens, and the outer shaft member does not make contact with the lens.

3. The insertion device according to claim 1, wherein the device is an intraocular-lens-preloaded type insertion device including the intraocular lens placed in a lens housing portion that is formed in the main body.

4. The insertion device according to claim 1, wherein said outer shaft member has a seal cap for sealing with said inner peripheral surface of said main body.

* * * * *